United States Patent
Spagnuolo et al.

(10) Patent No.: US 12,390,423 B2
(45) Date of Patent: Aug. 19, 2025

(54) AVOCATIN B FOR THE TREATMENT OF DISEASES AND CONDITIONS

(71) Applicant: SP NUTRACEUTICALS INC., Burlington (CA)

(72) Inventors: Paul Anthony Spagnuolo, Oakville (CA); Nawaz Ahmed, Kitchener (CA)

(73) Assignee: SP NUTRACEUTICALS INC., Burlington (CA)

( * ) Notice: Subject to any disclaimer, the term of this patent is extended or adjusted under 35 U.S.C. 154(b) by 829 days.

(21) Appl. No.: 17/642,068

(22) PCT Filed: Sep. 10, 2020

(86) PCT No.: PCT/CA2020/051220
§ 371 (c)(1),
(2) Date: Mar. 10, 2022

(87) PCT Pub. No.: WO2021/046646
PCT Pub. Date: Mar. 18, 2021

(65) Prior Publication Data
US 2023/0140688 A1    May 4, 2023

Related U.S. Application Data

(60) Provisional application No. 62/899,402, filed on Sep. 12, 2019.

(51) Int. Cl.
*A61K 31/047*  (2006.01)
*A61P 3/04*  (2006.01)
*A61P 3/08*  (2006.01)

(52) U.S. Cl.
CPC ............. *A61K 31/047* (2013.01); *A61P 3/08* (2018.01)

(58) Field of Classification Search
CPC ... C07C 33/025; C07C 33/042; A61K 31/047; A61P 3/04
See application file for complete search history.

(56) References Cited

U.S. PATENT DOCUMENTS

| | | | |
|---|---|---|---|
| 6,582,688 B1 | 6/2003 | Broutin | |
| 7,589,121 B2 | 9/2009 | Piccirilli | |
| 2009/0143279 A1 | 6/2009 | Mootha | |
| 2011/0217251 A1 | 9/2011 | Meretzki | |
| 2013/0216488 A1 | 8/2013 | Hernandez-Brenes | |
| 2014/0348967 A1 | 11/2014 | Msika | |
| 2015/0175933 A1 | 6/2015 | Segal | |
| 2017/0304251 A1 | 10/2017 | Spagnuolo | |

FOREIGN PATENT DOCUMENTS

| WO | 2008058269 | 5/2008 |
|---|---|---|
| WO | 2016054746 A1 | 4/2016 |

OTHER PUBLICATIONS

Examination Report under Section 18(3), application GB2204662.7 dated Oct. 20, 2022.
Lee, E. et al., "Targeting Mitochondria with Avocatin B Induces Selective Leukemia Cell Death", Cancer Res., vol. 75, No. 12, Jun. 15, 2015, 2478-2488.
International Preliminary Report on Patentability isssued in relation to PCT applicatino No. PCT/CA2020/051220, Mar. 15, 2022 (5 pages).
Foley, J. (Jun. 1992) "Rationale and Application of Fatty Acid Oxidation Inhibitors in Treatment of Diabetes Mellitus" Diabetes Care, vol. 15, No. 6, 773-784.
Hashimura, H. et al., (2001) "Acetyl-CoA Carboxylase Inhibitors from Avocado (Persea americana Mill) Fruits" Biosci. Biotechnol. Biochem., 65(7), 1656-1658.
Jump, B. et al., (2011) "Soraphen A, an inhibitor of acetyl CoA carboxylase activity, interferes with fatty acid elongation" Biochemical Pharmacology 81 pp. 649-660 DOI: 10.1016/j.bcp.2010.12.014.
Lopaschuk, Gary (2016) "Fatty Acid Oxidation and Its Relation with Insulin Resistance and Associated Disorders" Ann Nutr Metab ; 68 (suppl 3):15-20 DOI: 10.1159/000448357.
Navis, S. et al. (2016) "Ameliorating Effect of Avocado In Cardio-Metabolic Syndrome—A Review" World Journal of Pharmaceutical and Life Sciences, vol. 2, Issue 4, 100-109 ISSN 2454-2229.
Padmanabhan M. et al. (2015) "The modulating effect of Persea americana fruit extract on the levelof expression of fatty acid synthase complex, lipoprotein lipase, Pbroblast growth factor-21 and leptin Ð A biochemical study in ratssubjected to experimental hyperlipidemia and obesity", Phytomedicine J, Doi: 10.1016/j.phymed.2015.07.001.
Padmanabhan Monika and Geetha Arumugam. et al. (2016) "Effect of hydroalcoholic fruit extract of Persea americana Mill. on high fat diet induced obesity: A dose response study in rats", Indian Journal of Experimental Biology vol. 54, pp. 370-378.
Tabespour, J. et al. (2017) "Effects of Avocado (Persea americana) on Metabolic Syndrome: A comprehenvise Systematic Review", Phytotherapy Research DOI: 10.1002/ptr.5805.
Anderson, E. J. et al., (2009) "Mitochondrial H2O2 emission and cellular redox state link excess fat intake to insulin resistance in both rodents and humans", J. Clin. Invest. 119:573-581 doi: 10.1172/JCI37048.
Despres, J.P. et al., (2006) "Abdominal obesity and metabolic syndrome", Nature Publishing Group, vol. 444, pp. 881-887, doi: 10.1038/nature05488.
Muoio, D. M. et al., (2012) "Lipid-Induced Mitochondrial Stress and Insulin Action in Muscle", Cell Metabolism 15, pp. 595-605, DOI 10.1016/j.cmet.2012.04.010.
Randle, P.J. et al., (1963) "The Glucose Fatty-Acid Cycle Its Role In Insulin Sensitivity And The Metabolic Disturbances Of Diabetes Mellitus", The Lancet, pp. 785-789.
Goodpaster,.B.H et al., (2017) "Metabolic Flexibility in Health and Disease", Cell Metabolism 25, pp. 1027-1036, http://dx.doi.org/10.1016/j.cmet.2017.04.015.

(Continued)

*Primary Examiner* — Irina Neagu
(74) *Attorney, Agent, or Firm* — Joseph C. Zucchero; Carolyn S. Elmore; Elmore Patent Law Group, P.C.

(57) ABSTRACT

A method of treating a disease or condition may be characterized by a metabolic disorder in a subject in need thereof, that can include administering to the subject a therapeutically effective amount of avocatin B.

11 Claims, 12 Drawing Sheets

(56) References Cited

OTHER PUBLICATIONS

Randle, P.J. et al., (1998) "Regulatory Interactions between Lipids and Carbohydrates: The Glucose Fatty Acid Cycle After 35 Years", Diabetes/Metabolism Reviews, Diabetes Metab. Rev. 14, pp. 263-283.
Cline, G.W. et al., (1994) "13C-nuclear magnetic resonance spectroscopy studies of hepatic glucose metabolism in normal subjects and subjects with insulin-dependent diabetes mellitus.", J Clin Invest.; 94(6) pp. 2369-2376. https://doi.org/10.1172/JCI117602.
Kelley, D.E. et al., (1999) "Skeletal muscle fatty acid metabolism in association with insulin resistance, obesity, and weight loss", the American Physiological Society, pp. E1130-E1141.
Ciline, G.W. et al., (1997) "Mechanism of Impaired Insulin-stimulated Muscle Glucose Metabolism in Subjects with Insulin-dependent Diabetes Mellitus" J. Clin. Invest. vol. 99, 9, pp. 2219-2224.
Roden, M. et al., (1996) "Mechanism of Free Fatty Acid-induced Insulin Resistance in Humans", J. Clin. Invest., vol. 97, 12, 2859-2865.
Wolfe, R.R., (1998) "Metabolic interactions between glucose and fatty acids in humans", Am J Clin Nutr 67(suppl): pp. 519S-526S.
Koves, T.R., et al. (2006) "Mitochondrial Overload and Incomplete Fatty Acid Oxidation Contribute to Skeletal Muscle Insulin Resistance", Cell Metabolism 7, pp. 45-56.
Adams, S.H. et al., (2009) "Plasma Acylcarnitine Profiles Suggest Incomplete Long-Chain Fatty Acid b-Oxidation and Altered Tricarboxylic Acid Cycle Activity Type 2 Diabetic African-American Women", The Journal of Nutrition, pp. 1073-1081 DOI: 10.3945/jn.108.103754.
Mihalik, S.J. et al., (2010) "Increased Levels of Plasma Acylcarnitines in Obesity and Type 2 Diabetes and Identification of a Marker of Glucolipotoxicity", Obesity , vol. 18, pp. 1695-1700 doi: 10.1038/oby.2009.510.
Gavin, T. P. et al., (2018) "High Incomplete Skeletal Muscle Fatty Acid Oxidation Explains Low Muscle Insulin Sensitivity in Poorly Controlled T2D", J Clin Endocrinol Metab, 103(3):882-889, doi: 10.1210/jc.2017-01727.
Zhou, Y. et al., (1994) "Long-Term Exposure of Rat Pancreatic Islets to Fatty Acids Inhibits Glucoseinduced Insulin Secretion and Biosynthesis throughaGlucose Fatty Acid Cycle", J. Clin. Invest., 93:870-876.
Zhou Y. et al., (1995) "Palmitate-Induced (5-Cell Insensitivity to Glucose Is Coupled to Decreased Pyruvate Dehydrogenase Activity and Enhanced Kinase Activity in Rat Pancreatic Islets", Diabetes 44:394-399.
Biden, T.J. et al., (2004) "Chronic Effects of Fatty Acids on Pancreatic BetaB-Cell Function", Diabetes vol. 53 (Suppl. 1): pp. S159-S165.
Erion, K.A. et al., (2015) "Chronic Exposure to Excess Nutrients Left-shifts the Concentration Dependence of Glucose-stimulated Insulin Secretion in Pancreatic BetaB Cells", Journal of biological chemistry, vol. 290, 26, DOI 10.1074/jbc.M114.620351.
Jezek, P. et al., (2018) "Fatty Acid-Stimulated Insulin Secretion vs. Lipotoxicity", Molecules, vol. 23, 1483; 1-31 doi:10.3390/molecules23061483.
Muoio, D.M. et al., (2008) "Fatty Acid Oxidation and Insulin Action When Less Is More", Diabetes, vol. 57, pp. 1455-1456 DOI: 10.2337/db08-0281.
Keung, W. et al., "Inhibition of Carnitine Palmitoyltransferase-1 Activity Alleviates Insulin Resistance in Diet-Induced Obese Mice", Diabetes 1-10, Published online Nov. 8, 2012, Official publication as DIABETES, vol. 62, Mar. 2013, p. 711-720 DOI: 10.2337/db12-0259.
Gao, S. et al., (2015) "Therapeutic effects of adropin on glucose tolerance and substrate utilization in diet-induced obese mice with insulin resistance", Molecular Metabolism 4 pp. 310-324.
Collier, G.R. et al., (1993) "Effect of Fatty Acid Oxidation Inhibition on Glucose Metabolism in Diabetic Rats", Horm. metab. Res. 25 pp. 9-12.

Pettus, J. et al., (2016) "Effect of ranolazine on glycaemic control in patients with type 2 diabetes treated with either glimepiride or metformin", Diabetes, Obesity and Metabolism 18: pp. 463-474.
Buyukozturk, F. et al., (2009) "Impact of emulsion-based drug delivery systems on intestinal permeability and drug release kinetics", Journal of Controlled Release 142 pp. 22-30, doi: 10.1016/j.jconrel.2009.10.005.
Guo, Z. et al., (May 4, 2015) "Pyruvate dehydrogenase, Randle cycle, and skeletal muscle insulin resistance", PNAS Early Edition, www.pnas.org/cgi/doi/10.1073/pnas.1505398112.
Kelley, D.E. et al., (2005) "Skeletal muscle fat oxidation: timing and flexibility are everything", J. Clin. Invest., vol. 115, 7, pp. 1699-1702, doi: 10.1172/JCI25758.
Blaak, E. E. et al., (2006) "Fat Oxidation before and after a High Fat Load in the Obese Insulin-Resistant State", J Clin Endocrinol Metab 91 pp. 1462-1469.
Turner, N. et al., (2007) "Excess Lipid Availability Increases Mitochondrial Fatty Acid Oxidative Capacity in Muscle", Diabetes, vol. 56, pp. 2085-2092.
Ussher, J.R. et al., (2014) "Treatment with the 3-ketoacyl-CoA thiolase inhibitor trimetazidine does not exacerbate whole body insulin resistance in obese mice", The Jounal of Pharmacology and Experimental Therapeutics, vol. 349, Issue 3 pp. 487-496 DOI:10.1124/jpet.114.214197.
Defronzo, R.A. et al., (1981) "The Effect of Insulin on the Disposal of Intravenous Glucose", Diabetes, vol. 30, pp. 1000-1007.
Zou, C. et al., (2005) "2-NBDG as a fluorescent indicator for direct glucose uptake measurement", J. Biochem. Biophys. Methods 64 pp. 207-215, doi:10.1016/j.jbbm.2005.08.001.
Zhang, L. et al., (2010) "Role of fatty acid uptake and fatty acid β-oxidation in mediating insulin resistance in heart and skeletal muscle", Biochimica et Biophysica Acta 1801 pp. 1-22, doi: 10.1016/j.bbalip.2009.09.014.
Finck, B. N. et al., (2005) "A potential link between muscle peroxisome proliferatoractivated receptor-a signaling and obesity-related diabetes", Cell Meabolism, vol. 1, pp. 133-144 DOI 10.1016/j.cmet.2005.01.006.
Guerre-Millo, M. et al., (2001) "PPAR-a-Null Mice Are Protected From High-Fat Diet-Induced Insulin Resistance", Diabetes, vol. 50, pp. 2809-2814.
Dobbins, R.L. et al., (2001) "Prolonged Inhibition of Muscle Carnitine Palmitoyltransferase-1 Promotes Intramyocellular Lipid Accumulation and Insulin Resistance in Rats", Diabetes, vol. 50, pp. 123-130.
Bruce, R.B. et al., (2009) "Overexpression of Carnitine Palmitoyltransferase-1 in Skeletal Muscle Is Sufficient to Enhance Fatty Acid Oxidation and Improve High-Fat Diet-Induced Insulin Resistance", Diabetes, vol. 58, pp. 550-558.
Sebastian D. et al., (2007) "CPT I overexpression protects L6E9 muscle cells from fatty acid-induced insulin resistance", Am J Physiol Endocrinol Metab 292 pp. E677-E686, doi: 10.1152/ajpendo.00360.2006.
Iglesias, M.A. et al., (2002) "AICAR Administration Causes an Apparent Enhancement of Muscle and liver Insulin Action in Insulin-Resistant High-Fat-Fed Rats", Diabetes, vol. 51, pp. 2886-2894.
Abu-Elheiga, L. et al., (2003) "Acetyl-CoA carboxylase 2 mutant mice are protected against obesity and diabetes induced by high-fat/high-carbohydrate diets", PNAS, vol. 100, No. 10, pp. 10207-10212.
Carvajal-Zarrabal, O. et al., "Avocado Oil Supplementation Modifies Cardiovascular Risk Profile Markers in a Rat Model of Sucrose-Induced Metabolic Changes", Disease Markers, 2014:Article ID 386425, https://doi.org/10.1155/2014/386425, Feb. 25, 2014, 8 pgs.
Tabe, Y. et al., "Inhibition of F AO in AML cocultured with BM adipocytes: mechanisms of survival and chemosensitization to cytarabine", Scientific Reports, 8, https://doi.org/10.1038/s41598-018-35198-6, Nov. 15, 2018, 16837.
Uchenna, U. E. et al., "Inclusion of avocado (*Persea americana*) seeds in the diet to improve carbohydrate and lipid metabolism in rats", Rev. argent. endocrinol. metab., 54(3), Aug. 12, 2017, 140-148.

(56) References Cited

OTHER PUBLICATIONS

Henrique, C. et al., (2010) "Increased Mitochondrial Fatty Acid Oxidation Is Sufficient to Protect Skeletal Muscle Cells from Palmitate-induced Apoptosis", The Journal of Biological Chemistry, vol. 285, No. 47, pp. 36818-36827.

Hancock, C.R. et al., (2008) "High-fat diets cause insulin resistance despite an increase in muscle mitochondria", PNAS, vol. 105, No. 22, 7815-7820.

Bonnard, C. et al., (2008) "Mitochondrial dysfunction results from oxidative stress in the skeletal muscle of diet-induced insulin-resistant mice", J Clin Invest. , 118(2), pp. 789-800 https://doi.org/10.1172/JCI32601.

Andersen, P. et al., (1985) "Maximal Perfusion of Skeletal Muscle in Man", J. Physiol., 366, pp. 233-249.

Boushel, R. et al., (2007) "Patients with type 2 diabetes have normal mitochondrial function in skeletal muscle", Diabetologia, 50, pp. 790-796 DOI 10.1007/s00125-007-0594-3.

Holloway, G.P. et al., (2007) "Skeletal muscle mitochondrial FAT/CD36 content and palmitate oxidation are not decreased in obese women", Am J Physiol Endocrinol Metab 292: pp. E1782-E1789.

Timmers, S. et al., (2012) "Augmenting muscle diacylglycerol and triacylglycerol content by blocking fatty acid oxidation does not impede insulin sensitivity", PNAS, vol. 109, No. 29, p. 11711-11716 www.pnas.org/cgi/doi/10.1073/pnas.1206868109.

Holubarsch, C.J.F. et al. (2007) A double-blind randomised, multicentre clinical trial to evaluate the efficacy and safety of two doses of etomoxir in comparison with placebo in patients with moderate congestive heart failure: The ERGO (etomoxir for the recovery of glucose oxidation) study, Clinical Science, 113 (4), pp. 205-212.

Ussher, J.R. et al., (2016 ) "Genetic and pharmacological inhibition of malonyl CoA decarboxylase does not exacerbate age-related insulin resistance in mice", Diabetes (Publish Ahead of Print).

Batran, R.A. et al., (2019) "The antianginal ranolazine mitigates obesity-induced nonalcoholic fatty liver disease and increases hepatic pyruvate dehydrogenase activity", JCI Insight., 4(1), e124643 https://doi.org/10.1172/jci.insight.124643.

Spagnuolo, P., et al. research summary "Clinical development of avocado-derived lipids as modulators of fatty acid oxidation for the treatment and management of obesity and diabetes" posted by MITACS, Online at https://www.mitacs.ca/our-projects/clinical-development-of-avocado-derived-lipids-as-modulators-of-fatty-acid-oxidation-for-the-treatment-and-management-of-obesity-and-diabetes/ Believed to be published at least as early as Sep. 20, 2018 and last accessed Jan. 27, 2025.

Manning, Nick "Avocados may hold the answer to beating leukemia", Waterloo News, Jun. 15, 2015 (2 pages).

Hunt, Lori "Prof Receives Funding to Studay Avocado Compound as Potential Cancer Treatment" Jun. 2, 2017 (3 pages).

Ahmed, Nawaz (2018) "Analytical Method To Detect and Quantify Avocatin B in Hass Avocado Seed and Pulp Matter" J Nat Prod . Apr. 27, 2018;81(4):818-824. doi: 10.1021/acs.jnatprod.7b00914. Epub Mar. 22, 2018.

Lee, I-K, (2014) "The Role of Pyruvate Dehydrogenase Kinase in Diabetes and Obesity" Diabetes Metab J 2014;38:181-186, http://dx.doi.org/10.4093/dmj.2014.38.3.181.

Dai L. et al., "Oxidative stress and calcium dysregulation by palmitate in type 2 diabetes" Experimental & Molecular Medicine (2017) 49, e291; doi:10.1038/emm.2016.157; published online Feb. 3, 2017.

Boucher, J., et al., (2014) "Insulin Receptor Signaling in Normal and Insulin-Resistant States" Cold Spring Harb. Perspect. Biol. 6.

Steggall, A., Mordi, I., Lang, C., (May 10, 2017) "Targeting Metabolic Modulation and Mitochondrial Dysfunction in the Treatment of Heart Failure" Diseases 2017, 5, 14.

AVOCATIN B FOR THE TREATMENT OF DISEASES AND CONDITIONS

CROSS-REFERENCE TO RELATED APPLICATION

This application is a National Stage entry of International Application No. PCT/CA2020/051220, filed Sep. 10, 2020, which claims priority to and the benefit of U.S. provisional application No. 62/899,402 filed Sep. 12, 2019 and entitled Avocatin B for the treatment of diseases and conditions, the entirety of which is incorporated herein by reference.

FIELD OF THE INVENTION

The present disclosure relates generally to diet-induced obesity, and more particularly to treating diet-induced obesity and associated pathologies with avocatin B.

BACKGROUND

U.S. Patent publication no. 2017/0304251 discloses a method of treating a leukemia comprising administering to a subject in need thereof a therapeutically effective amount of a composition comprising a compound of Formula (I) and/or (II), and/or isomers, stereoisomers or solvates thereof and/or mixtures thereof.

SUMMARY OF THE INVENTION

The teachings described herein may, in one broad aspect, relate to a method of treating a disease or condition characterized by dysregulation of glucose-stimulated insulin secretion (GSIS) in a subject in need thereof, the method comprising administering to the subject a therapeutically effective amount of avocatin B.

The teachings described herein may, in another broad aspect, relate to a method of treating a disease or condition characterized by a metabolic disorder in a subject in need thereof, the method comprising administering to the subject a therapeutically effective amount of avocatin B.

In another of its aspects, the teachings described herein may relate to a method of treating a disease or condition characterized by insulin resistance in a subject in need thereof, the method comprising administering to the subject a therapeutically effective amount of avocatin B.

In another of its aspects, the teachings described herein may relate to a method of treating a disease or condition characterized by reduced insulin sensitivity in a subject in need thereof, the method comprising administering to the subject a therapeutically effective amount of avocatin B.

In another of its aspects, the teachings described herein may relate to a method of rescuing glucose-stimulated insulin secretion (GSIS) in a subject having obesity associated lipotoxicity, the method comprising administering to the subject a therapeutically effective amount of avocatin B.

In another of its aspects, the teachings described herein may relate to a method of increasing glucose utilization in a subject in need thereof, the method comprising administering to the subject a therapeutically effective amount of avocatin B.

In another of its aspects, the teachings described herein may relate to a method of modulating reactive oxygen species in a subject in need thereof, the method comprising administering to the subject a therapeutically effective amount of avocatin B.

In another of its aspects, the teachings described herein may relate to a method of increasing glucose uptake in pancreatic tissue in a subject in need thereof, the method comprising administering to the subject a therapeutically effective amount of avocatin B.

In another of its aspects, the teachings described herein may relate to a method of increasing glucose uptake in skeletal muscle tissue in a subject in need thereof, the method comprising administering to the subject a therapeutically effective amount of avocatin B.

In another of its aspects, the teachings described herein may relate to a method of increasing glucose oxidation in pancreatic tissue in a subject in need thereof, the method comprising administering to the subject a therapeutically effective amount of avocatin B.

In another of its aspects, the teachings described herein may relate to a method of increasing glucose oxidation in skeletal muscle tissue in a subject in need thereof, the method comprising administering to the subject a therapeutically effective amount of avocatin B.

In another of its aspects, the teachings described herein may relate to a method of reversing insulin resistance in a subject in need thereof, the method comprising administering to the subject a therapeutically effective amount of avocatin B.

In another of its aspects, the teachings described herein may relate to a method of increasing insulin sensitivity in a subject in need thereof, the method comprising administering to the subject a therapeutically effective amount of avocatin B.

Other aspects of the teachings described herein, which may be used in combination with any other aspect, including the broad aspect listed above, may include that the disease or condition is diet-induced obesity.

The therapeutically effective amount of avocatin B may be administered in at least one daily dose.

The at least one daily dose may comprise from about 25 mg to about 200 mg of avocatin B.

The at least one daily dose may comprise about 50 mg of avocatin B.

The teachings described herein may, in another broad aspect, relate to use of a therapeutically effective amount of avocatin B for treating a disease or condition characterized by a metabolic disorder in a subject in need thereof.

The metabolic disorder may be characterized by dysregulation of glucose-stimulated insulin secretion (GSIS) in the subject.

The metabolic disorder may be characterized by insulin resistance in the subject.

The metabolic disorder may be characterized by reduced insulin sensitivity in the subject.

The metabolic disorder may be characterized by obesity associated lipotoxicity in the subject.

In another of its aspects, the teachings described herein may further comprise increasing glucose utilization in the subject.

In another of its aspects, the teachings described herein may further comprise modulating reactive oxygen species in the subject.

In another of its aspects, the teachings described herein may further comprise increasing glucose uptake in pancreatic tissue in the subject.

In another of its aspects, the teachings described herein may further comprise increasing glucose uptake in skeletal muscle tissue in the subject.

In another of its aspects, the teachings described herein may further comprise increasing glucose oxidation in pancreatic tissue in the subject.

In another of its aspects, the teachings described herein may further comprise increasing glucose oxidation in skeletal muscle tissue in the subject.

In another of its aspects, the teachings described herein may further comprise reversing insulin resistance in the subject.

In another of its aspects, the teachings described herein may further comprise increasing insulin sensitivity in the subject.

The teachings described herein may, in another broad aspect, relate to a pharmaceutical composition comprising a therapeutically effective amount of avocatin B and a carrier.

The therapeutically effective amount may comprise from about 25 mg to about 200 mg.

The therapeutically effective amount may comprise about 50 mg.

Thus, the present inventors have developed a novel therapy for DIO and associated pathologies. By exploiting fatty acid metabolism, this therapy can be used to improve metabolic complications associated with DIO and lipotoxicity. In particular, this treatment can be provided after DIO to improve glucose tolerance, glucose utilization, and insulin sensitivity. The present therapeutic use may provide a well-tolerated treatment option with a clinically acceptable safety profile in the treatment of DIO and associated metabolic disorders.

Other advantages of the invention will become apparent to those of skill in the art upon reviewing the present specification.

BRIEF DESCRIPTION OF THE DRAWINGS

Embodiments of the present disclosure will be described with reference to the accompanying drawings, wherein like reference numerals denote like parts, and in which.

Figure 6:
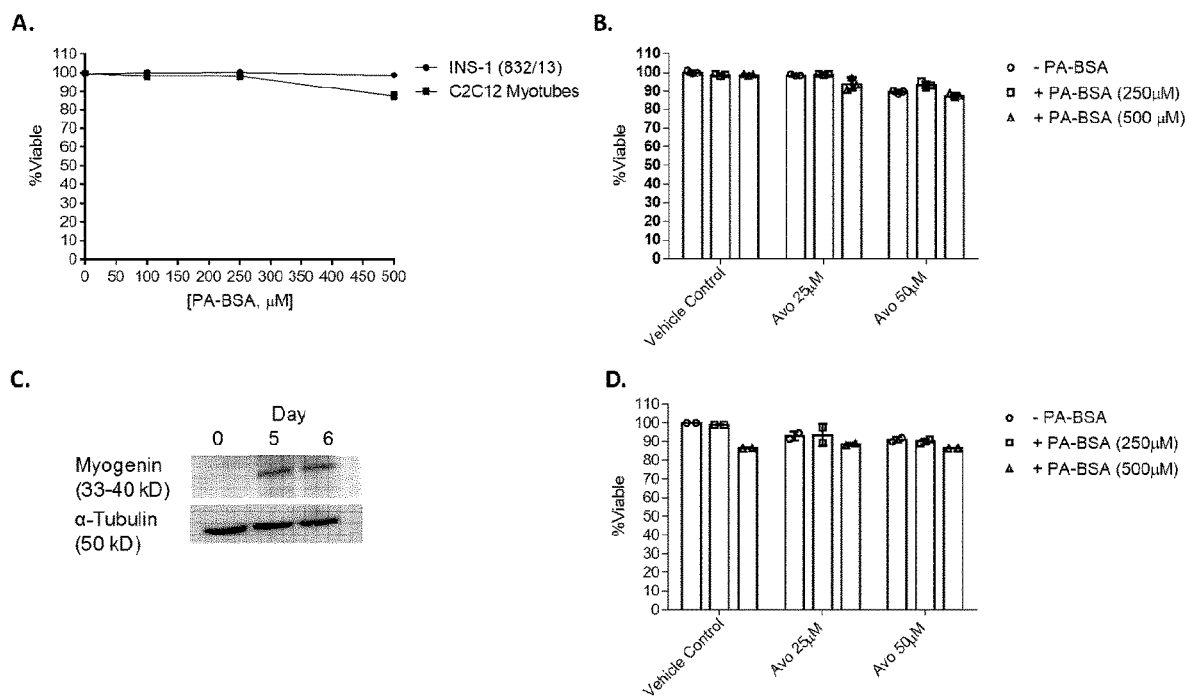
Figure 7:
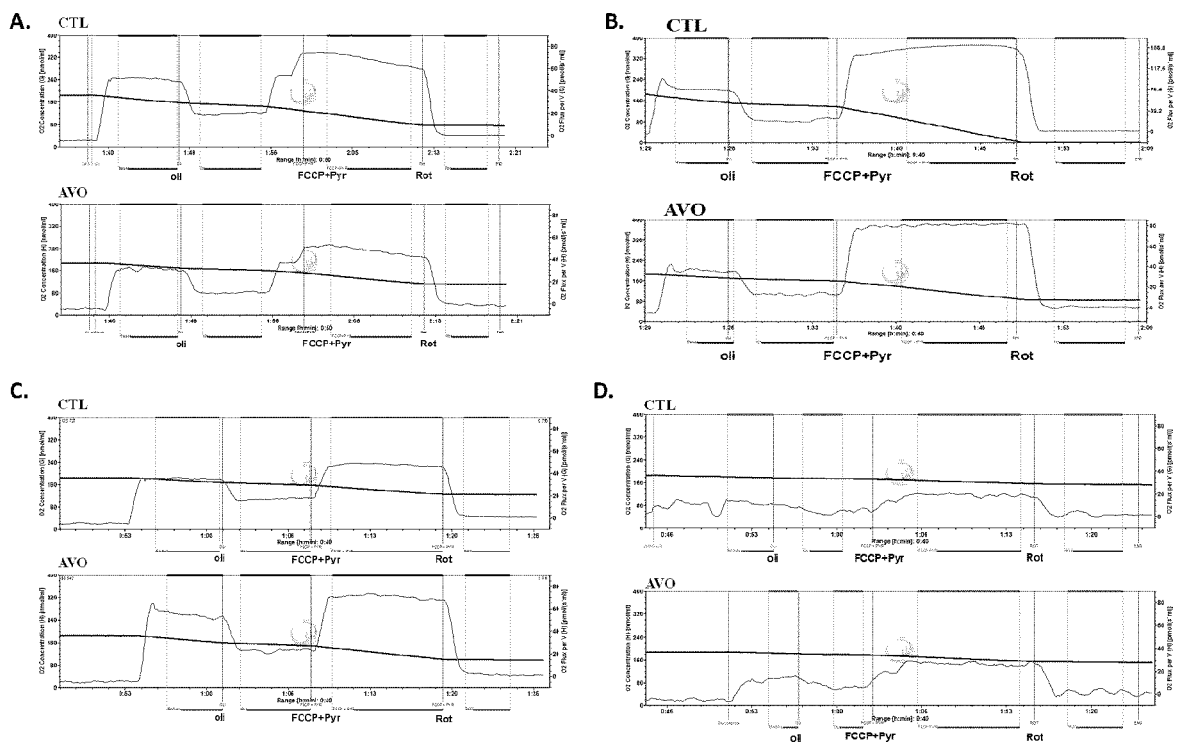
Figure 8:
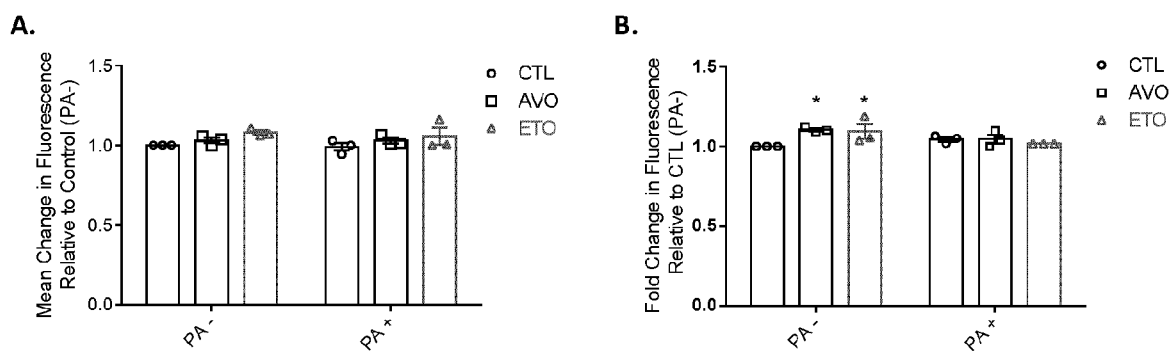
Figure 9:
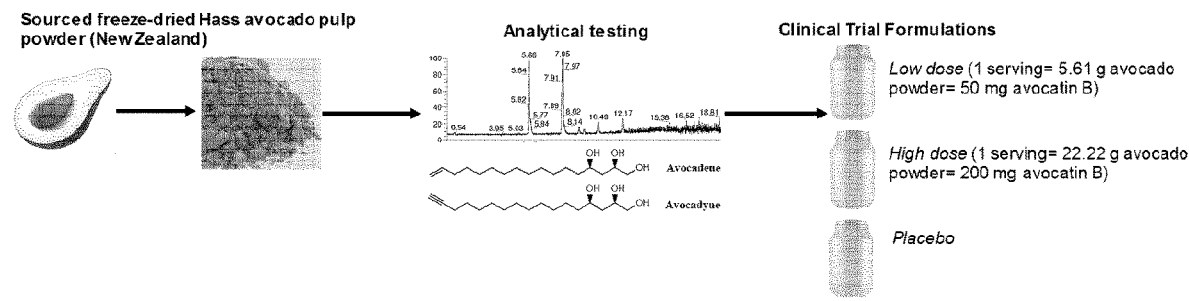
Figure 10:
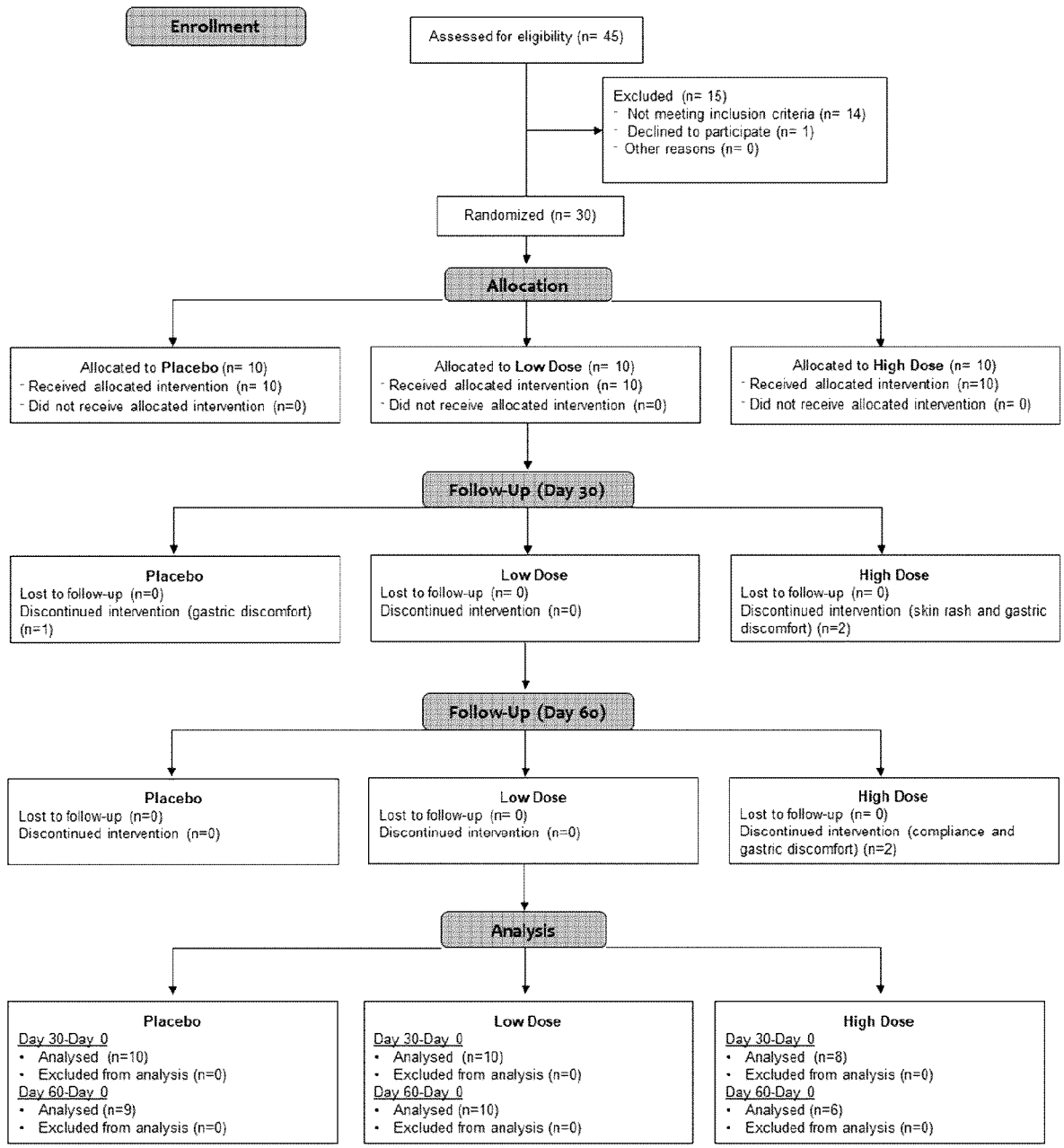

Hemoglobin. (B) Hematocrit. (C) Red blood cells (RBC). (D) White blood cells. (E) Neutrophils. (F) Lymphocyte. (G) Eosinophils. (H) Basophils. (1) Platelets. N=3-5/group, one-way ANOVA with Tukey's post hoc test;

FIG. 6 illustrates cell viability assessments. (A) INS-1 (832/13) cells or day five C2C12 myotubes were treated for 24 h with 0.5% BSA/1 mM L-carnitine (Control) or 0.1-0.5 mM palmitate-BSA/1 mM L-carnitine in low glucose media (5.5 mM) after which cell viability was measured via flow cytometry using propidium iodide. (B) INS-1 (832/13) cells were treated for 24 h with 25 or 50 µM avocatin B in the absence or presence of 0.25 or 0.5 mM palmitate-BSA/1 mM L-carnitine after which cell viability was measured via flow cytometry using propidium iodide. (C) C2C12 cells were differentiated in differentiation media for 5-6 days, lysed and collected for Western Blot analysis of myogenin (skeletal muscle specific protein). (D) Day 5 C2C12 myotubes were treated for 24 h with 25 or 50 µM avocatin B in the absence or presence of 0.25 or 0.5 mM palmitate-BSA/1 mM L-carnitine after which cell viability was measured via flow cytometry using propidium iodide. All data represents mean±S.D. N=2;

FIG. 7 illustrates High resolution respirometry (HRR) example oxygraphs. (A-B) PA-BSA supported respiration was measured in (A) INS-1 (832/13) cells or (B) day 5 C2C12 myotubes by treating with FAO inhibitors (avocatin B or etomoxir) in the presence of 0.25 mM PA-BSA for 24 h after which cells were trypsinized, collected and injected into the respirometer. (C-D) To assess metabolic flexibility, (C) INS-1 (832/13) cells or (D) day 5 C2C12 myotubes were treated with FAO inhibitors and PA-BSA as previously described, after which cells were trypsinized, collected and subject to a 15 min incubation with 10 mM D-glucose before being washed and injected into the respirometer;

FIG. 8 illustrates Mitochondrial mass determination. INS-1 (832/13) (A) or C2C12 myotubes (B) were treated for 24 h with 0.5% BSA/1 mM L-carnitine (Control), or 0.5 mM palmitate-BSA/1 mM L-carnitine (PA), or PA+25 µM AVO (AVO+PA), or PA+100 µM etomoxir (ETO+PA), or AVO or ETO alone in low glucose media (5.5 mM). Cells were then collected and stained with NAO dye for mitochondrial mass determination. Data represents means±SEM from three independent experiments, *p<0.05; vs PA− or PA+ control group, Dunnett's post hoc test;

FIG. 9 illustrates a method of preparation for avocatin B clinical trial formulations;

FIG. 10 illustrates the CONSORT participant flow diagram; and

Figure 11:
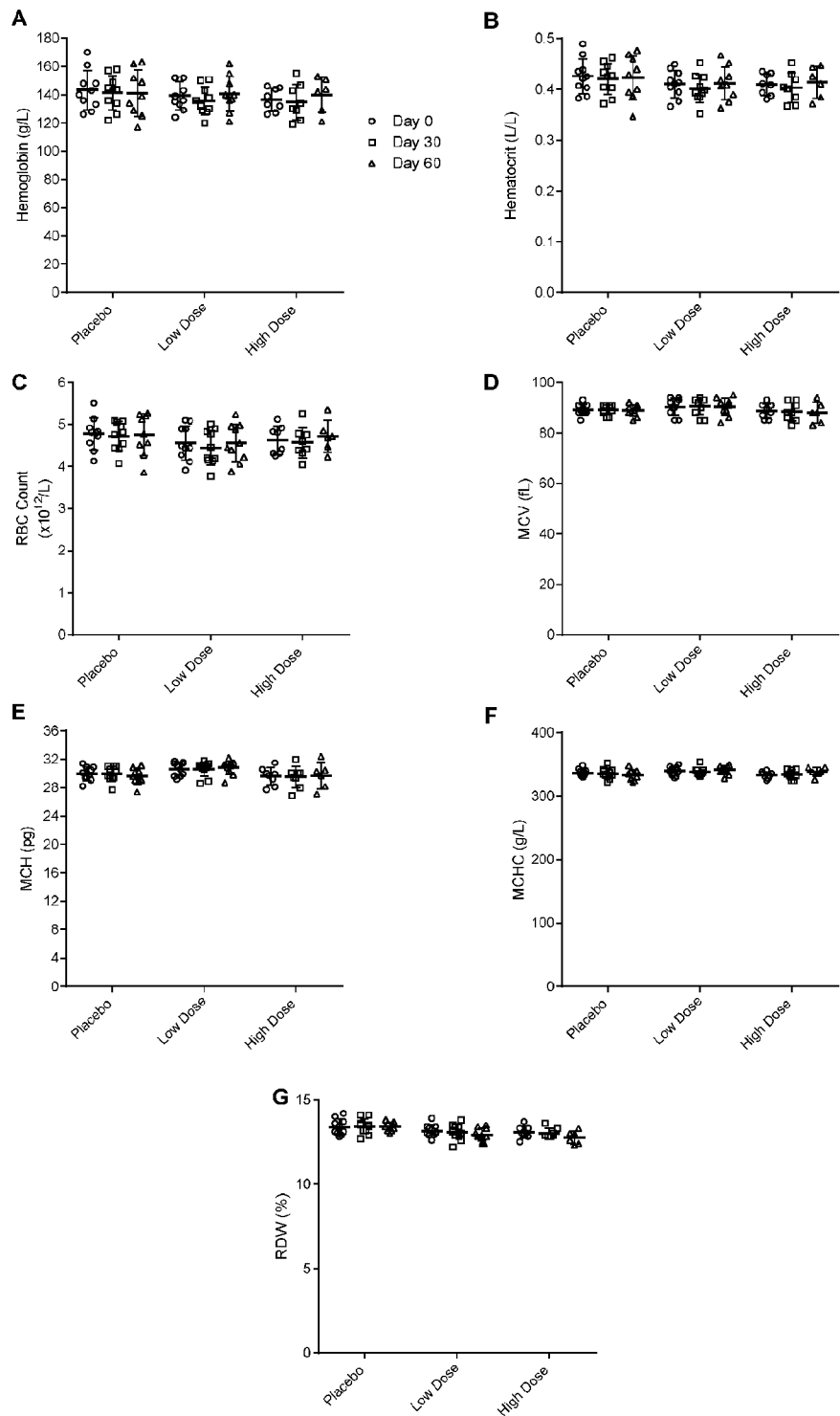
Figure 11:
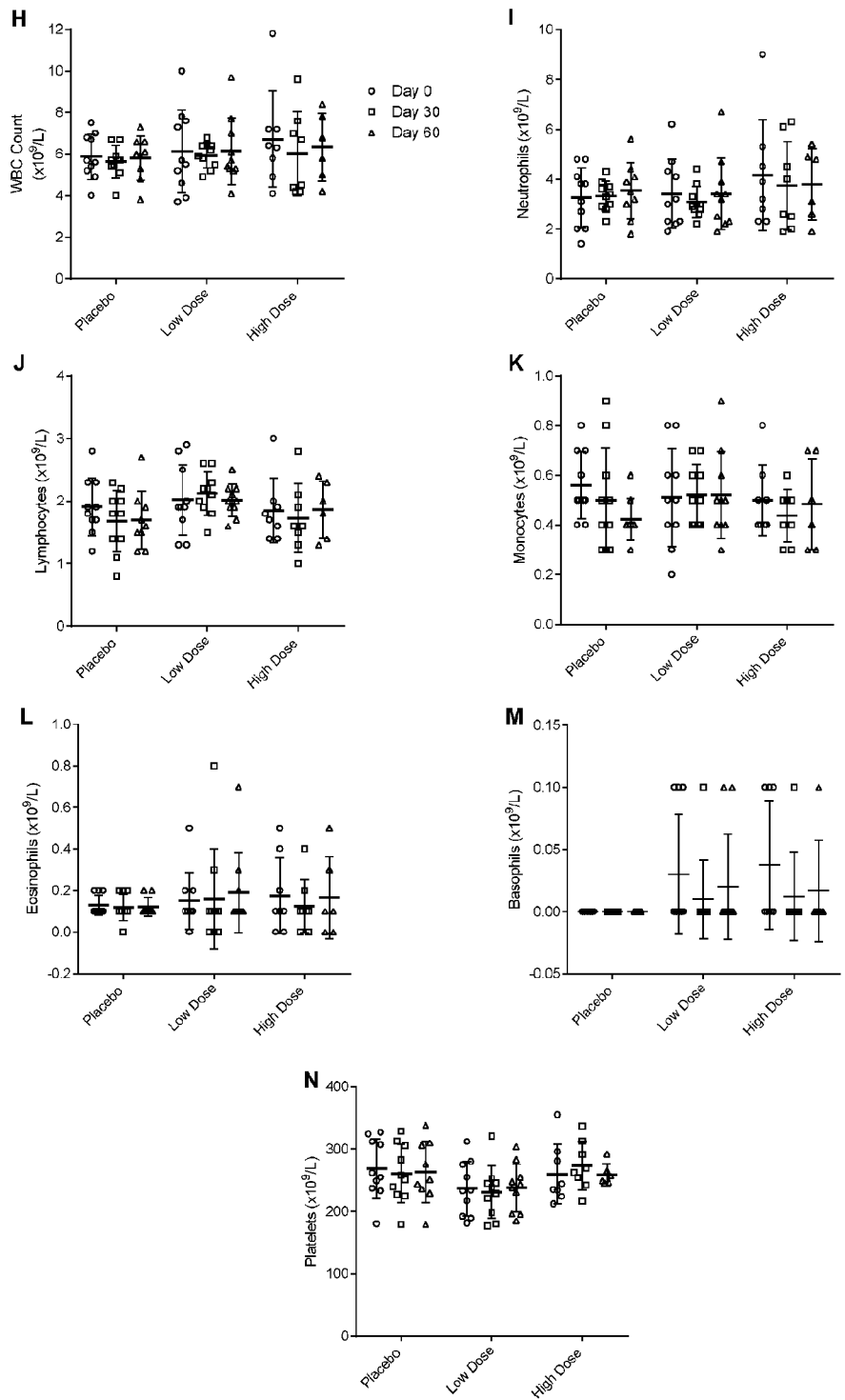

FIG. 11 illustrates a complete blood count with differential (CBC w/diff) analysis on whole blood collected from all clinical trial participants on day 0, day 30, and day 60 (endpoint). (A) Hemoglobin. (B) Hematocrit. (C) Red blood cells (RBC). (D) Mean corpuscular volume. (E) Mean corpuscular hemoglobin. (F) Mean corpuscular hemoglobin concentration. (G) Red cell distribution width. N=3-10/group, Kruskal-Wallis—One-Way Analysis of Variance on Ranks. (H) White blood cells. (I) Neutrophils. (J) Lymphocytes. (K) Monocytes. (L) Eosinophils. (M) Basophils. (N) Platelets.

DETAILED DESCRIPTION

Various uses or methods will be described below to provide an example of an embodiment of the claimed invention. No embodiment described below limits any claimed invention and any claimed invention may cover uses or methods that differ from those described below. The claimed inventions are not limited to uses or methods having all of the features of any one use or method described below or to features common to multiple or all of the uses or methods described below. It is possible that a use or method described below is not an embodiment of any claimed invention. Any invention disclosed in a use or method described below that is not claimed in this document may be the subject matter of another protective instrument, for example, a continuing patent application, and the applicants, inventors or owners do not intend to abandon, disclaim, or dedicate to the public any such invention by its disclosure in this document.

Diet-induced obesity (DIO) is a central risk factor for the onset of metabolic complications like insulin resistance, type 2 diabetes (T2D), and cardiovascular diseases[1-3].

The mechanism(s) by which lipotoxicity (i.e., elevated free fatty acids, FFAs) causes metabolic dysfunction continue to be debated. For example, Randle and colleagues[4] reported that metabolic flexibility, which is the capacity of tissues to adapt fuel oxidation to substrate availability[5], can be impaired in obese and diabetic patients. Based on this, Randle[6] proposed that insulin resistance may be driven by elevated rates of skeletal muscle fatty acid oxidation (FAO; or β-oxidation). In support of this, it has been reported that transgenic mice engineered to increase flux through FAO develop insulin resistance, whereas transgenic mice with limited FAO capacity challenged with high-fat diets (HFDs) have normal insulin sensitivity[12, 38, 39]. Moreover, HFDs have been reported to cause insulin resistance in rodents while increasing skeletal muscle mitochondrial biogenesis and β-oxidation[33, 46], where induced alterations in skeletal muscle mitochondrial structure and function occur only after the onset of insulin resistance[47].

Other studies have pointed to nutrient overload causing pathologies as a result of high rates of incomplete FAO (that produce lipotoxic acyl carnitines) and/or increases in oxidative stress (i.e., excessive ROS production)[1, 12]. Incomplete mitochondrial FAO has been reported to be a factor in skeletal muscle insulin resistance, with excess β-oxidation in the post-prandial state giving rise to incomplete FAO, which produces lipotoxic acylcarnitines that impair carbohydrate utilization, depletes organic intermediates of the tricarboxylic acid (TCA) cycle, and generates reactive oxygen species (ROS)[12-15].

Others have challenged the link between insulin resistance and elevated rates of FAO[7-11]. For example, accelerating FAO as a means to process excess FFAs has been proposed as a therapeutic strategy to overcome nutrient overload[40-45]. These studies have questioned the traditional view of the Randle Cycle in skeletal muscle and have suggested that impaired glucose oxidation may be a direct result of defective insulin stimulated glucose uptake, neither of which is related to increased FAO[10, 11].

In the pancreas, the site of insulin synthesis and secretion, lipotoxicity has been reported to disrupt the glucose-fatty acid cycle in β-cells[16, 17], which was reported to impair glucose-stimulated insulin secretion (GSIS), resulting in hyperinsulinemia in vitro and in vivo[16, 18-20]. In addition, skeletal muscle oxidative capacity has been reported to be in excess of the energy demands of resting muscle[48] and despite reductions in mitochondrial content observed in obese and diabetic patients, insulin-resistant skeletal muscle have been reported to have normal mitochondrial function[49, 50].

Despite the advances made to date in the development of treatment for DIO and associated pathologies, there is room for improvement to address the above-mentioned problems and shortcomings.

It is an object of the present disclosure to obviate or mitigate at least one of the above-mentioned disadvantages, and to provide a novel therapy for DIO and associated pathologies.

FAO has been reported to be modifiable through drug-targeting and pharmacological agents that directly or indirectly inhibit FAO have shown a wide-range of protective benefits in DIO[24, 25, 34, 53]. As such, inhibiting FAO may be a potential therapeutic strategy in DIO[21-27]; however, to date, safe and well-tolerated small molecules that effectively target this metabolic pathway are lacking. For example, while ETO has been used an inhibitor of FAO, it can impart dose-limiting toxicities[51, 52]. Such dose-limiting toxicities prevent the clinical use of most FAO inhibitors. Ranolazine, a partial FAO inhibitor used to treat angina, was recently approved for use in combination therapies for obesity and diabetes; however; its beneficial activity is primarily in the liver via a mechanism not related to FAO[27, 34, 54]. Moreover, these pharmacological agents have no reported activity in pancreatic tissue, the site of insulin secretion.

Lee et al. reported that the avocado-derived lipid, avocatin B (AvoB), is an FAO inhibitor that can accumulate in mitochondria to induce leukemia cell apoptosis without imparting toxicity toward normal cells[28]. However, there are differences between leukemia cells from other, normal cells that may affect their behaviour. For example, leukemia cells may have higher mitochondrial mass (see PMID: 22094260) and altered metabolic features that distinguish them from normal cells such as a greater reliance on oxidative phosphorylation (22094260), amino acid metabolism (30753831); and fatty acid oxidation (20038799). Therefore, targeting these metabolic perturbations may have different effects on different cell types and may, for example, result in leukemia cell death and not death in normal cells (22094260; 30420752; 30753831; 23333149; 31287994; 29892070).

EXPERIMENTAL EXAMPLES

Preferred embodiments of the present disclosure will be described with reference to the following exemplary information which should not be used to limit or construe the invention.

Methods

Pre-Clinical Mouse Studies

For the treatment study, twelve-week-old male C57BL/6J mice were purchased from Jackson Laboratory (Bar Harbor, ME) and allowed to acclimatize for 1 week. After acclimatization, mice received either a high-fat diet (HFD) (60% kcal from lard; Research Diet D12492; Research Diets, USA) or a standard diet (10-13% kcal from fat; Teklad 2014; Envigo, USA) for eight weeks. At the end of week eight, animals continued on their respective diets but were administered AvoB (100 mg/kg body weight—b.w.) or vehicle via gavage twice weekly for 5 weeks (see FIG. 1A). AvoB was formulated in a self-emulsifying drug delivery system (SEDDS) as previously described[29] where the oil phase (comprised of surfactant and oil) was less than 10% (v/v) of the final oil-in-water emulsion. Animal weights were monitored twice weekly. At study completion, animals were euthanized (10-12 h into their dark cycle) via $CO_2$ followed by exsanguination, after which tissue and blood was collected.

Glucose and Insulin Tolerance Tests

Intraperitoneal glucose and insulin tolerance tests (GTT and ITT) were performed 8 hours after food withdrawal. For GTT, a glucose dose of 1.5 g/kg was used for mice on both HFD and standard diet. For ITT, an insulin (Humulin, Eli Lilly, USA) dose of 1 U/kg and 0.25 U/kg was used for mice on HFD and standard diet, respectively. Blood glucose levels were determined at 0, 10, 20, 30, 60, and 90 minutes after glucose/insulin administration via tail bleed using the OneTouch Blood Ultra 2 glucose meters (LifeScan Europe, Switzerland).

Measurement of Complete Blood Counts, Plasma and Tissue Biochemical Markers

Complete blood count with differential (CBC w/diff) analysis was done on 500 µL of whole blood by the animal health laboratory at the University of Guelph. Plasma insulin, FFAs, and triacylglycerols (TAGs) were measured using a rat/mouse insulin ELISA kit (Millipore, Rat/Mouse Insulin Detection kit), FFA fluorometric assay kit (Cayman, MI, USA), and the TAG colorimetric assay kit (Cayman, MI, USA), respectively. Manufacturer's protocols were followed for all kits.

Insulin Resistance Index (HOMA-IR) Calculations

The homeostasis model assessment was used to calculate the insulin resistance (HOMA-IR) index[60] using the values of fasting plasma glucose (FPG) and fasting plasma insulin (FPI) as follows: with FPG expressed as mg/dL and PI as mU/L; HOMA-IR=FPGxFPI/22.5, with FPG expressed as mmol/L and FPI as mIU/L.

Pyruvate Dehydrogenase (PDH) Activity Assay

After mice were euthanized, muscle tissues were freeze-clamped and flash-frozen in liquid nitrogen. The PDH activity from flash-frozen whole gastrocnemius muscle lysates was measured using a colorimetric microplate assay kit (ab109902, Abcam, Cambridge, MA, USA) following the manufacturer's protocol and as previously described (see reference number 12). Briefly, PDH proteins from whole gastrocnemius muscle lysates (lysed in the presence of 10 mM sodium fluoride (NaF) preserve the phosphorylated status of PDH or to determine native PDH activity as a result of HFD feeding) were immunocaptured on a microplate by loading equal amounts of protein for each sample. PDH activity was then determined spectrophotometrically by monitoring the reduction of NAD+ to NADH, coupled to the reduction of a reporter dye at an absorbance of 450 nm.

All animal studies were carried in accordance to the regulations of the Canadian Council on Animal Care (CCAC) and with the approval of the Animal Care Committee at the University of Guelph.

In Vitro Studies

Cell Culture

Cells were cultured in a humidified atmosphere containing 5% $CO_2$ at 37° C. INS-1 (832/13) rat pancreatic β-cell line was cultured in in RPMI 1640 medium containing 11.1 mM glucose and supplemented with 10% fetal bovine serum (FBS), 1% penicillin/streptomycin, 2 mM L-glutamine, 1 mM sodium pyruvate, and 50 µM p-mercaptoethanol. INS-1(832/13) cells are a robust p-islet cell culture model routinely used given their glucose responsiveness and endogenous insulin production. C2C12 mouse skeletal myoblast were cultured in growth media consisting of low-glucose Dulbecco's Modified Eagles Medium (DMEM; Hyclone, ThermoFisher) supplemented with 10% FBS and 1% penicillin/streptomycin. Differentiation of C2C12 myoblasts into myotubes was induced by switching 90% confluent cells to differentiation media consisting of low-glucose DMEM supplemented with 2% horse-serum and 1% penicillin/streptomycin. Differentiation media was changed every 24 h for up to 5 days prior to all experimental treatments. At day 5 of the differentiation process, myoblasts are fully converted into myotubes, as determined by morphological assessment and immunoblotting for myogenin, a skeletal muscle-specific protein (FIG. 6C).

Cell Viability

Quantitative analysis of cell death was evaluated by flow cytometry using propidium iodide staining (Biovision, Mountainview, CA), where specified, according to the manufacturer's protocol and as previously described[28]. Viable cells were identified as PI negative (PI−).

High Resolution Respirometry

Cells treated with test compounds for 24 h were trypsinized, counted, and resuspended in phosphate buffer saline (PBS). High-resolution $O_2$ consumption measurements were conducted in 2 ml of respiration medium (PBS, pH 7.5, stir speed 750 rpm) using the Oroboros Oxygraph-2k (Oroboros Instruments, Corp., Innsbruck, Austria) set to 37° C. with a gain of 2 in both chambers. Briefly, after the injection of 5 million treated INS-1 (832/13) cells or C2C12 myotubes per chamber, basal respiration was measured once steady-state respiratory flux was obtained; this represents coupled respiration fueled by available substrates from the incubation with test compounds. Uncoupled respiration was then measured following addition of the ATP synthase inhibitor oligomycin (0.25 µM). This was followed by measuring maximal respiratory rate by stepwise titration of carbonyl cyanide p-trifluoromethoxy phenyl hydrazone (FCCP; within 0.1-0.25 µM) in the presence of 1 mmol/L pyruvate. Finally, respiration was inhibited by addition of rotenone (0.5 µM; complex I inhibitor) to obtain extra-mitochondrial residual oxygen consumption. Data was recorded with DatLab software (Oroboros Instruments, Innsbruck, Austria), oxygen consumption at each step of the protocol was normalized to vehicle control and illustrated in histograms. For all HRR protocols, cell viability was determined after trypsinization and also after end of HRR runs via trypan blue cell staining and counting using a hemocytometer. No significant differences in cell viability between control and treated cells were observed.

C2C12 myoblasts or INS-1 (832/13) cells were treated in low glucose media with AvoB (25 µM) or etomoxir (100 µM) in the presence of 0.25 mM PA/1 mM carnitine for 24 h before being collected and injected into the respirometer to assess PA supported respiration. Additionally, to indirectly assess metabolic flexibility, cells were treated the same way as described, collected and subjected to a 15 min treatment of 10 mM D-glucose before being washed and injected into the respirometer; these experiments were done to assess if cells incubated in low glucose/high fat conditions for 24 h can easily switch to glucose utilization upon acute incubation with D-glucose.

Fatty Acid Oxidation

FAO in cell lines was determined using established methods. Briefly, cells were pretreated with AvoB (25 µM) or etomoxir (100 µM) in the presence of 0.5 mM PA/1 mM L-carnitine for 24 h after which they were washed with PBS and subject to radiolabeled $[1-^{14}C]$-palmitate for 3 h. $[1-^{14}C]$-palmitate was prepared and applied to cells as follows: purchased stock supplied in ethanol (PerkinElmer, MA, USA) was dried in vacuo and then re-suspended in a solution containing unlabeled carrier in BSA to yield a mixture of 7% BSA [w/v], 2.5 mM palmitate with $[1-^{14}C]$-palmitate at a final concentration of 10 µCi/mL. Following a 16 hour incubation at 37° C., the solution containing radiolabeled palmitate was diluted with respective serum free cell culture media (low glucose RPMI media for INS-1 (832/13) cells and low glucose DMEM for C2C12 myotubes) containing 1 mM L-carnitine to a final concentration of 0.3% BSA, 100 µM palmitate, and 0.4 µCi/mL $[1-^{14}C]$-palmitate. Following incubation of treated cells with $[1-^{14}C]$-palmitate, 400 µL of well media was transferred to acidification vials containing perchloric acid and capped with $CO_2$ filter traps impregnated with 1M NaOH. The vials were then incubated at room temperature for one hour to allow for $CO_2$ capture and precipitation of undigested palmitate. The $CO_2$ trap was transferred to scintillation vials containing 4 mL of scintillation fluid and complete FAO was quantified using a Tri-Carb 2910 TR liquid scintillation analyzer (PerkinElmer). The amount of radioactivity in the media was also determined after pelleting cells and debris (14,000×g, 10 min); this quantified acid soluble metabolites (ASMs), an indirect measure of incomplete FAO.

Glucose Oxidation and Uptake

C2C12 myotubes and INS-1 (832/13) cells treated as in the FAO assays described above and then incubated with D-$[^{14}C(U)]$-glucose (0.58 µCi/mL) and unlabeled glucose (final glucose concentration 200 µM) for 4 h subsequent to which $[^{14}C]$—$CO_2$ (representing complete glucose oxidation) and ASMs (representing incomplete glucose oxidation) were captured and quantified as described in the FAO method. For C2C12 myotubes, glucose oxidation and uptake was measured with and without a 30 min pre-incubation with 100 nM insulin to determine basal and insulin-mediated glucose oxidation or uptake, respectively.

To measure glucose uptake in C2C12 myotubes, a fluorescent D-glucose analog 2-(N-[7-nitrobenz-2-oxa-1,3-diazol-4-yl]amino)-2-deoxy-D-glucose (2-NBDG) was utilized. Briefly, myotubes were treated for 24 h with test compound after which they were washed twice with PBS and starved for 1 h in serum and glucose free DMEM. Following starvation, 100 nM insulin was added for 30 min after which 60 µM 2-NBDG was added to each well and allowed to incubate for 30 min. The 2-NBDG uptake reaction was then stopped by removing the incubation medium and washing the cells twice with PBS after which the cells were trypsinized and collected for flow cytometry analysis (Guava 8HT; EMD Millipore, Billerica, MA).

Glucose Stimulated Insulin Secretion (GSIS) in INS-1 (832/13) Cells

To measure glucose stimulated insulin secretion (GSIS) in INS-1(832/13) cells a standard protocol was adopted. Briefly, cells were grown to 80% confluency in 6 well plates and treated with AvoB or etomoxir with or without palmitate as described for the FAO assay. After treatments were complete, cell media was replaced with KRB (Krebs-Ringer Bicarbonate) buffer. Cells were then challenged with 3 mM glucose for 2 h in KRB buffer after which 500 µL KRB buffer was collected and frozen in −80° C. until analysis. For another 2 h, cells were challenged with 16 mM glucose after which 500 µL KRB was collected and frozen in −80° C. until analysis. The amount of insulin released into the KRB buffer was determined by an ELISA kit (Millipore, Rat/Mouse Insulin Detection kit). Data was normalized for cellular protein content, as determined by the Micro-BCA Protein Assay kit. The glucose-dependent insulin secretory index ($GSIS_{16/3}$), defined as the ratio between the insulin secretion at 16 mM (stimulatory, surrogate to postprandial glucose levels) and 3 mM (basal, surrogate to fasting glucose levels) glucose was also calculated.

Reactive Oxygen Species, Mitochondrial Membrane Potential, and Mitochondrial Mass Determination For all ROS studies, INS-1 (832/13) cells and C2C12 myotubes were treated with or without palmitate and FAO inhibitors for 24 h in low glucose cell culture media as described for the FAO assay. After treatment, cells were trypsinized and re-suspended in PBS containing 5 µM of the fluorescent dye MitoSOX® (Molecular Probes, Invitrogen) and allowed to incubate for 5-15 minutes in a humidified atmosphere containing 5% $CO_2$ at 37° C. Cells were then washed in PBS, placed in a 96 well plate and fluorescence was measured by flow cytometry. ROS was quantified by normalizing the mean fluorescence values of live gated cells to vehicle control. Mitochondrial membrane potential (MMP) in INS-1 (832/13) and C2C12 myotubes was measured using the cationic fluorescent dye JC-1 (Molecular Probes). JC-1 accumulates in the mitochondrial matrix in an MMP dependent manner. JC-1 fluoresces green in the cytosol where it exists as a monomer, after entering the mitochondria JC-1 monomers form J aggregates and fluoresce red, thus the red/green fluorescence ratio is used to determine MMP. After all treatments, cells were washed, trypsinized and re-suspended in PBS containing 1 µM JC-1 and allowed to incubate for 5-10 minutes in a humidified atmosphere containing 5% $CO_2$ at 37° C. Cells were then washed in PBS, placed in a 96 well plate and fluorescence was measured by flow cytometry. MMP was quantified by normalizing the mean fluorescence values of live gated cells to vehicle control. Mitochondrial mass was measured using 10-N-nonyl acridine orange (NAO; Enzo Life Sciences, ENZ-52306), which accumulates in the mitochondria in an MMP-independent manner where it binds to cardiolipin in the inner mitochondrial membrane. Cells were treated, washed and collected as described and incubated with 0.35 µM NAO and green fluorescence was measured using flow cytometry. In all analysis (ROS, MMP and mitochondrial mass), forward vs side scatter plots were gated to exclude debris (e.g., dead cells), as cell death is associated with increased ROS and altered membrane potentials.

Cellular ATP Content

Total cellular ATP content was determined using the ATP bioluminescent assay kit (Calbiochem, 119107). Briefly, cells were seeded in white walled 96-well plates ($1.2 \times 10^4$ cells/well for INS-1 and $2 \times 10^4$ cells/well for C2C12) and treated for 24 h (C2C12 cells were differentiated for 5 days prior to treatments whereas INS-1 cells were treated 24 h after seeding). After treatment, culture media was removed, and cells were lysed with nucleotide releasing buffer with gentle shaking for 5 min. ATP monitoring enzyme was then added to cell lysates and plates and luminescence was read in a Biotek Synergy HT spectrophotometer (Biotek; Winooski, VT).

Cytosolic Calcium Determination

INS-1 (832/13) cells were treated as described for the FAO assays but also with metabolic modulators dichloroacetate (DCA) (1 mM) and trimetazidine (25 µM) as well as 10 µM endoplasmic reticulum calcium blocker 8-(N,N-Diethylamino)-octyl-3,4,5-trimethoxybenzoate HCl (TMB-8) (Sigma Aldrich) or 25 nM cyclosporin (Sigma Aldrich) in the presence of 0.5 mM palmitate/1 mM L-carnitine. Cytosolic calcium was measured in INS-1 (832/13) cells using fluo-3AM (Invitrogen, F1241) charged fluorescent dye that accumulates in the cytosol and emits green fluorescence after binding calcium ions. A stock solution of 10 mM fluo-3AM was diluted to 5 µM in fluo-3AM loading buffer (10 mM 4-(2-hydroxyethyl)-1-piperazineethanesulfonic acid (HEPES), 137 mM NaCl, 5 nM KCl, 1 mM Na2HPO4, 5 mM glucose, and 0.5 mM MgCl2 (pH 7.4)]. After treatment, cells were incubated in fluo-3AM loading buffer for 30 min at 37° C. with gentle agitation after which cells were washed twice with PBS, trypsinized and collected for flow cytometry analysis. Cytosolic calcium was quantified by taking the mean green fluorescence values of live gated cells and normalizing to vehicle control.

Immunoblotting Analysis

For all cell culture experiments, after drug treatments cells were washed with chilled phosphate-buffered saline (PBS), and lysed in chilled lysis buffer with 1× protease inhibitor cocktail (Sigma). RIPA lysis buffer (Sigma-Aldrich) was used for INS-1 (832/13) cells and muscle lysis buffer for C2C12 myotubes (20 mM HEPES, 10 mM NaCl, 1.5 mM MgCl2, 1 mM DTT, 20% glycerol, and 0.1% Triton-X100). Cells were scraped, mechanically homogenized using a syringe and centrifuged at 14,000×g for 20 min at 4° C. and the supernatants were collected. For preparation of all gastrocnemius muscle lysates, 10 mg frozen tissue (wet weight) was washed in chilled PBS, placed in a dounce homogenizer, lysed in muscle lysis buffer and centrifuged at 14,000×g for 20 min at 4° C. and the supernatant was collected. Protein content for cell and tissue lysates was measured using the BCA protein assay kit (ThermoFisher) according to manufacturer's protocol. Thirty µg protein lysates were prepared in loading buffer and immunoblotting was performed by heating lysates for 5 minutes at 95° C. and subjecting them to gel electrophoresis on 10% SDS-polyacrylamide gels at 150 V for 75 minutes. Using a semi-dry transfer apparatus (Bio-Rad) the gels were then transferred at 25V for 45 minutes to a PVDF membrane and blocked with 5% BSA (Sigma) in tris-buffered saline-tween (TBS-T) for 1 hour. The membrane was incubated overnight with the target primary antibody and a loading control (GAPDH or α-tubulin) primary antibody (1:15000 or 1:1000; ThermoFisher) at 4° C. The following primary antibodies were used at the specified dilutions: $pAKT^{Ser473}$ (9271, 1:500, 60 kDa), AKT (9272, 1:1000, 60 kDa), pAMPKα-Thr172 (2531, 1:500, 62 kDa), AMPKα (2532, 1:1000, 62 kDa), pERK1/2-Thr202/Tyr204 (4370, 1:500, 42 and 44 kDa), Erk1/2 (4695, 1:1000, 42 and 44 kDa), pP38-Thr180/Tyr182 (4511, 1:500, 43 kDa), and P38 (8690, 1:1000, 40 kDa) was purchased from Cell Signaling Technology, myogenin (F5D, 1:200, 34 kDa) was purchased from Developmental Studies Hybridoma Bank, PGC-1α (ab54481, 1:500, 105 kDa) and CPT1A (ab128568, 1:500, 88 kDa) were purchased from Abcam. PVDF Membranes were then washed and incubated with the appropriate horseradish peroxidase—(HRP) conjugated secondary antibody (1:3000) for 1 hour at room temperature. Bands were visualized using clarity enhanced chemiluminescence (ECL) substrates (Bio-Rad) and the ChemiGenius 2 Bio-Imaging System (Syngene). The approximate molecular weight for each protein was estimated using Precision Plus Protein WesternC ladder (Bio-Rad) that was electrophoresed and transferred onto the membrane.

Statistical Analysis

Unless otherwise stated, in vitro results are presented as mean±SEM whereas in vivo results are presented as mean±SD. Data were analyzed with GraphPad Prism 6.0 (GraphPad Software, USA) using one or two-way ANOVA with Bonferroni's or Dunnett's post hoc analysis for between group comparisons. Standard student's t-tests were also used where appropriate. $P<0.05$ was accepted as being statistically significant. Normality for all data sets was verified by using the Shapiro-Wilk normality test on Graph- Pad Prism 6.0 and non-parametric tests were used to analyze some data as specified in their figure legends.

Avocatin B Oral Consumption Pilot Clinical Study

A single center, double-blind, placebo-controlled, randomized, pilot clinical study was executed to determine the safety of consuming 50 mg (equivalent to consuming a quarter Hass avocado pulp) or 200 mg (equivalent to consuming one Hass avocado pulp) AvoB per day for 60 days in healthy human participants (NCT03898505).

AvoB and Placebo Supplement Preparation

The investigational product was approved by Health Canada (natural product number (NPN) 80074296). To create the product, freeze-dried avocado pulp powder was sourced from Avocado Oil New Zealand Ltd., (Tauranga, New Zealand) and tested for absolute quantities of AvoB per gram of powder using a validated analytical method[61]. Clinical trial material was then standardized to contain low dose (50 mg) or high dose (200 mg) AvoB (FIG. 9). The placebo product was formulated similarly to the investigational product except it only contained the non-medicinal food-grade ingredients used in the test product and other excipients that were used to simulate appearance, smell, texture and taste of the investigational product. Participants in every group consumed 40 g of material per day for 60 days by dissolving/blending the product in 12-16 ounces of a smoothie like diluent (e.g., milk (with or without lactose), soy milk, coconut milk, or fruit juice of the participant's choice). All three products were approximately matched for total calories per serving.

Table 1 summaries the nutritional composition of each product, setting out the macro-and-micro nutrient composition of the AvoB clinical trial formulations

TABLE 1

| Component | Placebo | Low dose | High dose |
|---|---|---|---|
| Calories (kcal) | 83 | 130 | 147 |
| Protein (g) | 3.2 | 4.4 | 2.9 |
| Total Fat (g) | 4.2 | 7.1 | 9.4 |
| Saturated (g) | 0.8 | 1.3 | 1.4 |
| Carbohydrates (g) | 5.5 | 8.2 | 7.8 |
| Dietary Fibre (g) | 2.3 | 3.8 | 4.8 |
| Sodium (mg) | 153 | 179 | 23.5 |
| Cholesterol (g) | 0 | 0 | 0 |
| Potassium (mg) | 306 | 563 | 869 |

1.3.2. Study Participants and Study Objectives

Healthy volunteers (13 males and 17 females; age range 20-54 years, BMI range 19.1-29.9) were enrolled in the study. Exclusion criteria were: presence of active clinical disease and history of diabetes, hypertension, dyslipidemia, major depressive disorders, chronic liver disorders, kidney disorders, or blood disorders. Volunteers that were pregnant, had history of previous bariatric surgery, or were actively using prescription or non-prescription medications that impact weight gain or loss were also excluded. Baseline characteristics of participants are highlighted in Table 1. All participants provided written informed consent for enrollment in the study and for taking part in all study related protocols. Primary outcome was the analysis of adverse experiences (AEs) measured throughout the study. Secondary outcomes were to ascertain safety and tolerability which were assessed through clinically relevant changes in standard laboratory evaluations (blood chemistry and hematology) measured on days 0, 30 and 60. Body mass index (BMI) and glycated hemoglobin (HbA1c) were also measured as part of secondary outcomes. Laboratory evaluations included serum alanine aminotransferase (ALT) to assess liver function; serum creatinine to assess kidney function; serum creatine phosphokinase to assess muscle injury; total serum bilirubin to assess blood cell lysis, complete blood count to assess overall health, and HbA1c as part of secondary outcomes. All AEs were rated by the study investigators for intensity and relationship to study drug as outlined in the Common Terminology Criteria for Adverse Events (CTCAE) version 5.0. All blood collection and analysis was completed at a private diagnostic laboratory (LifeLabs, Canada).

1.3.3. Statistical Analysis

Mean change from baseline at day 30 and 60 for all laboratory evaluations and body weight were analysed by the non-parametric Kruskal-Wallis—One-Way Analysis of Variance on Ranks. using GraphPad Prism 6.0 (GraphPad Software, USA) where differences with $p<0.05$ were considered to be statistically significant. AEs were tabulated (for all randomized patients who received at least one dose of study supplements) and analyzed using Fisher's exact test of independence in Statistical Analysis System (SAS) university edition where differences with $p<0.05$ were considered to be statistically significant.

All study protocols were approved by the research ethics board (REB) at the University of Guelph and Health Canada Natural and Non-prescription Health Products Directorate (NNHPD).

Results

Figure 1:
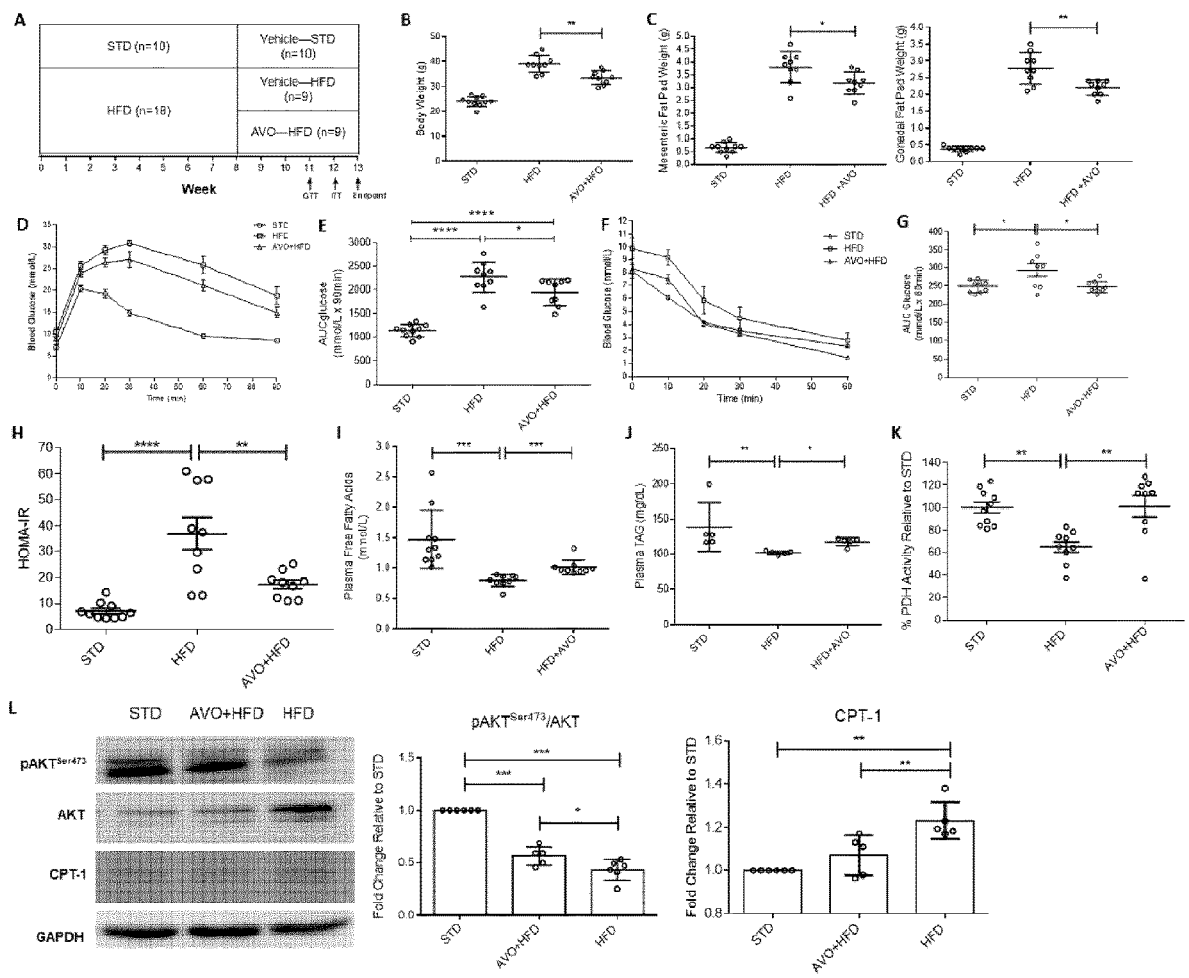
FIG. 1 illustrates the effects of avocatin B (AvoB) in a mouse model of DIO. (A) Treatment study design schematic. Mice (N=28) received either a high-fat diet (HFD) or a low-fat standard diet (STD) for 8 weeks. At the end of week 8, mice were randomly divided into three groups: (i) vehicle-STD (STD); n=10, (ii) vehicle-HFD (HFD); n=9, and (iii) HFD mice treated with 100 mg/kg b.w., AVO twice weekly (HFD+AVO; n=9). STD and HFD mice were treated with vehicle-control twice weekly. (B) Mouse weights at treatment study termination (week 13). (C) Gonadal (left) and mesenteric (right) fat pads (GFP and MFP) were excised and weighed upon study termination. (D) Effect of AVO on glucose tolerance. For GTT, an i.p. glucose injection was administered, after which blood glucose levels were monitored at regular intervals for 90 min. (E) Area under the curve (AUC) calculated for the glucose excursion curve of the GTT. (F) Effect of AVO on whole body insulin sensitivity. For ITT, an i.p. insulin injection was administered, after which blood glucose levels were monitored at regular intervals for 60 min. (G) AUC calculated for the glucose excursion curve of the ITT. (H) HOMA-IR index, a measure of insulin resistance, was calculated as described in the methods section. (1) Plasma free fatty acids and (J) plasma triacylglycerols (TAG) was measured at endpoint from ad libitum animals. (K) Native pyruvate dehydrogenase (PDH) activity in whole gastrocnemius muscle lysates in the presence of phosphatase inhibitors was measured. (L) Phosphorylation of Akt-Ser$^{473}$ (a marker of insulin signaling) and CPT-1A enzyme protein levels were assessed via western blot on gastrocnemius muscle lysates from ad libitum animals. Figure shows representative western blots for pAkt-Ser$^{473}$ total AKT, CPT-1A, and GAPDH (loading control); histograms (right) represent fold change in pAkt-Ser$^{473}$ and CPT-1A levels relative to STD mice. For (B-C) data presented as mean weight±S.D., *$p<0.05$, **$p<0.01$, unpaired, two-tailed, student's t-test. For (E, G, H and K) data represents mean S.D., N=8-10/group. *$p<0.05$, $p<0.01$; * $p<0.001$, one-way ANOVA, Bonferroni's post hoc test. For (I-J) data represents mean±S.D., N=9-10/group for I and n=5 for J, *$p<0.05$, $p<0.01$; * $p<0.001$, Mann-Whitney U test. For (L) data represents mean±S.D. N=5-6/group, $p<0.01$; * $p<0.001$, one-way ANOVA, Bonferroni's post hoc test.
Figure 5:
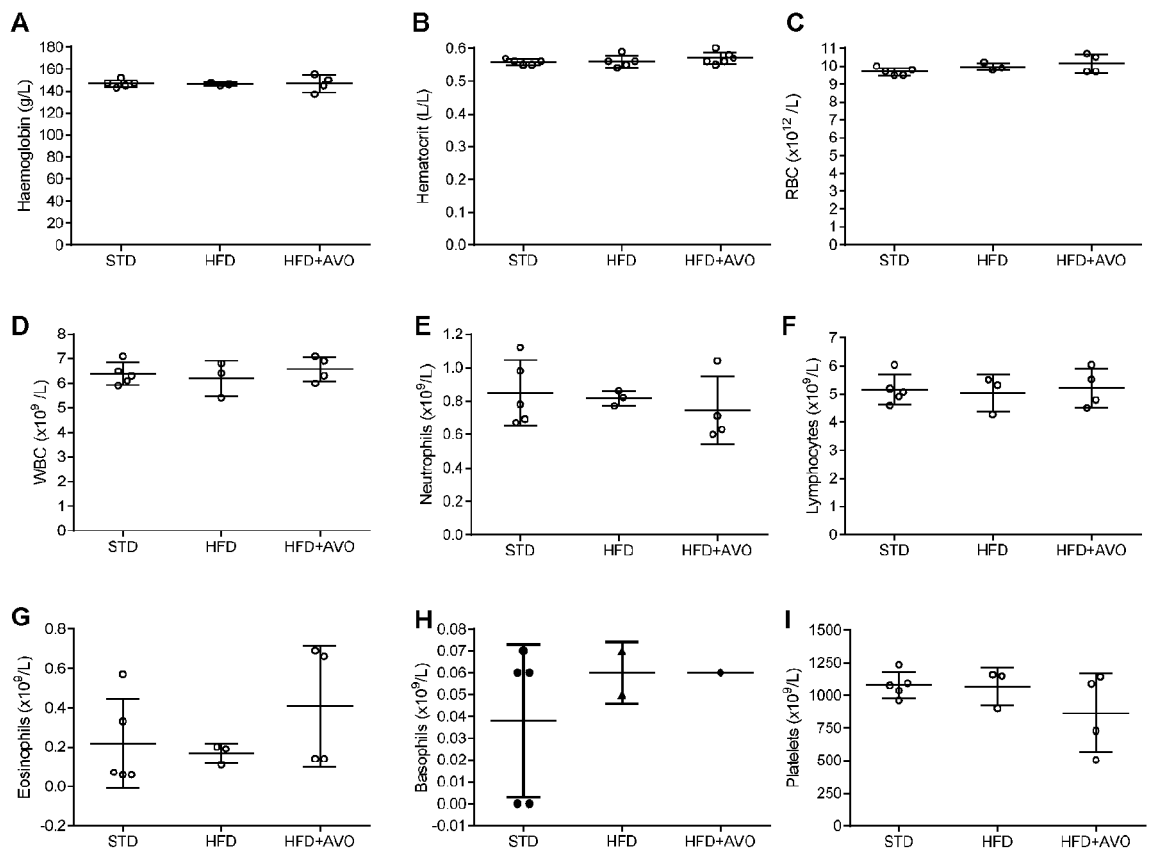
FIG. 5 illustrates the complete blood count with differential (CBC w/diff) analysis on whole blood collected from 3-5 animals per group at treatment-DIO study endpoint. (A)

AvoB Inhibits FAO and Improves Glucose Tolerance and Insulin Sensitivity after DIO is Established in Mice AvoB was first assessed in vivo in a conventional treatment model of DIO. C57BL/6J mice were given a standard (STD; 10-13% kcal from fat) or high fat diet (HFD; 60% kcal from fat) for a total of 12 weeks. At week 8, AvoB (100 mg/kg b.w.) or vehicle control was administered by oral gavage twice weekly for a total of 5 weeks (FIG. 1A). At study completion, HFD mice treated with AvoB weighed significantly less than HFD-control mice (FIG. 1B; $t(16)=3.84$, $p<0.01$) demonstrating reductions in both gonadal and mesenteric fat pad (GFP and MFP) weights (FIG. 1C: GFP: $t(16)=3.34$; $p<0.01$; MFP: $t(16)=2.50$; $p<0.05$). AvoB had no effect on blood markers of toxicity (FIG. 5). HFD mice treated with AvoB had significantly improved glucose tolerance compared to HFD-control mice (FIGS. 1D and E; $F(2,25)=51.27$; $p<0.0001$) and also had greater insulin sensitivity (FIGS. 1F and G; $F(2,23)=6.37$; $p<0.01$). The homeostasis model assessment index for insulin resistance (HOMA-IR; an index of insulin action) was increased in HFD-control mice (FIG. 1H) whereas AvoB-treated-HFD mice had HOMA-IR index values comparable to lean, STD mice (FIG. 1H; $F(2,25)=17.22$; $p<0.0001$). AvoB treatment also increased plasma levels of FFA (FIG. 1I; $U=0$, $p<0.001$) and triacylglyercols (TAG) (FIG. 1J; $U=0$, $p<0.001$) in ad libitum mice compared to control-HFD ad libitum mice, which together are indirect indicators of decreased whole body FAO and increased glucose utilization as has been previously reported [24, 25, 31]. The plasma FFA and triacylglycerol levels of ad libitum lean mice on standard diets were observed to be higher than HFD-mice due to significant differences in carbohydrate and fat content of the two diets.

The activity of muscle pyruvate dehydrogenase (PDH; a mitochondrial enzyme that facilitates pyruvate oxidation to acetyl-CoA) is suppressed in DIO due to excessive FAO which impairs the balance between fatty acid and glucose oxidation [30]. Given its role in the measure of metabolic flexibility in obese and diabetic patients [31, 32] and in mouse models of DIO [33], native PDH activity was quantified in skeletal muscle excised from ad libitum mice at endpoint was quantified. HFD-control mice had decreased gastrocnemius muscle PDH activity consistent with elevated FAO. In contrast, PDH activity in AvoB-treated-HFD mice was restored to that of lean, STD mice (FIG. 1K; $F(2,25)=9.235$, $p<0.001$) suggesting higher glucose oxidation in AvoB-treated-HFD mice. In addition to higher PDH activity, AvoB-treated-HFD mice also had increased phosphorylation of AKTSer473, a key marker of insulin signaling, in gastrocnemius muscle compared to HFD-control mice (FIG. 1L). Furthermore, HFD-control mice had higher post-prandial glucose utilization in AVO-treated-HFD mice and higher protein levels of CPT-1A in gastrocnemius muscle compared to AVO-treated-HFD mice, which eludes to higher rates of FAO in HFD-control mice (FIG. 1L). Collectively, these results suggest AvoB inhibited whole body FAO and altered skeletal muscle substrate preference from fatty acids to glucose thereby reversing insulin resistance in a treatment model of DIO.

AvoB Inhibits FAO During Lipotoxicity in Pancreatic β-Islet Cells which Improves Glucose Stimulated Insulin Secretion To determine the mechanism by which AvoB ameliorates mitochondrial lipid overload (i.e., lipotoxicity), the ability of AvoB to inhibit FAO in pancreatic β-cells (INS-1 (832/13) was examined. This was done in the presence of excess lipids that cause mitochondrial dysfunction but not cell death (i.e., >250 μM palmitate-BSA (PA-BSA) with 1 mM L-carnitine for 24 h; herein referred to as lipotoxic conditions (FIG. 6). In β-cells, AvoB inhibited complete FAO, as determined by measuring [1-$^{14}$C]-palmitate oxidation to $CO_2$ (FIG. 2A; $F(3,16)=46.76$; $p<0.0001$), and did not increase levels of acid soluble metabolites (ASM), an indicator of incomplete FAO (FIG. 2A; $F(1,16)=55.59$; $p<0.0001$). FAO inhibition under lipotoxic conditions was also tested using high resolution respirometry (HRR) where AvoB inhibited palmitate supported basal and maximal-uncoupled respiration in INS-1 (832/13) cells (FIG. 2B; $F(6,24)=14.44$; $p<0.0001$; see FIG. 7A for example HRR oxygraphs). AvoB imparted this activity at concentrations four-fold lower than etomoxir (ETO), a conventional FAO inhibitor used as a positive control, and had no effect on cell viability (FIG. 6A).

To determine whether AvoB-induced inhibition of FAO could increase glucose utilization in INS-1 cells, oxidation of D-[$^{14}$C(U)]-glucose to $CO_2$ was measured. Under lipotoxic conditions, AvoB caused greater glucose oxidation compared to cells treated with palmitate only (FIG. 2C; $F(3,8)=77.25$, $p<0.0001$). We confirmed this effect using HRR, where β-cells were incubated under high fat/low glucose conditions in the presence or absence of AvoB for 24 h and then challenged with 10 mM glucose for 15 min prior to injection into the respirometer. Addition of glucose, in the presence of AvoB, increased basal and maximal respiration compared to the palmitate-only control (FIG. 2D; $F(2,24)=10.81$; $p<0.0004$; see 7C for HRR oxygraphs). These results demonstrate that AvoB inhibits FAO and increases glucose utilization in pancreatic tissue.

Figure 2:
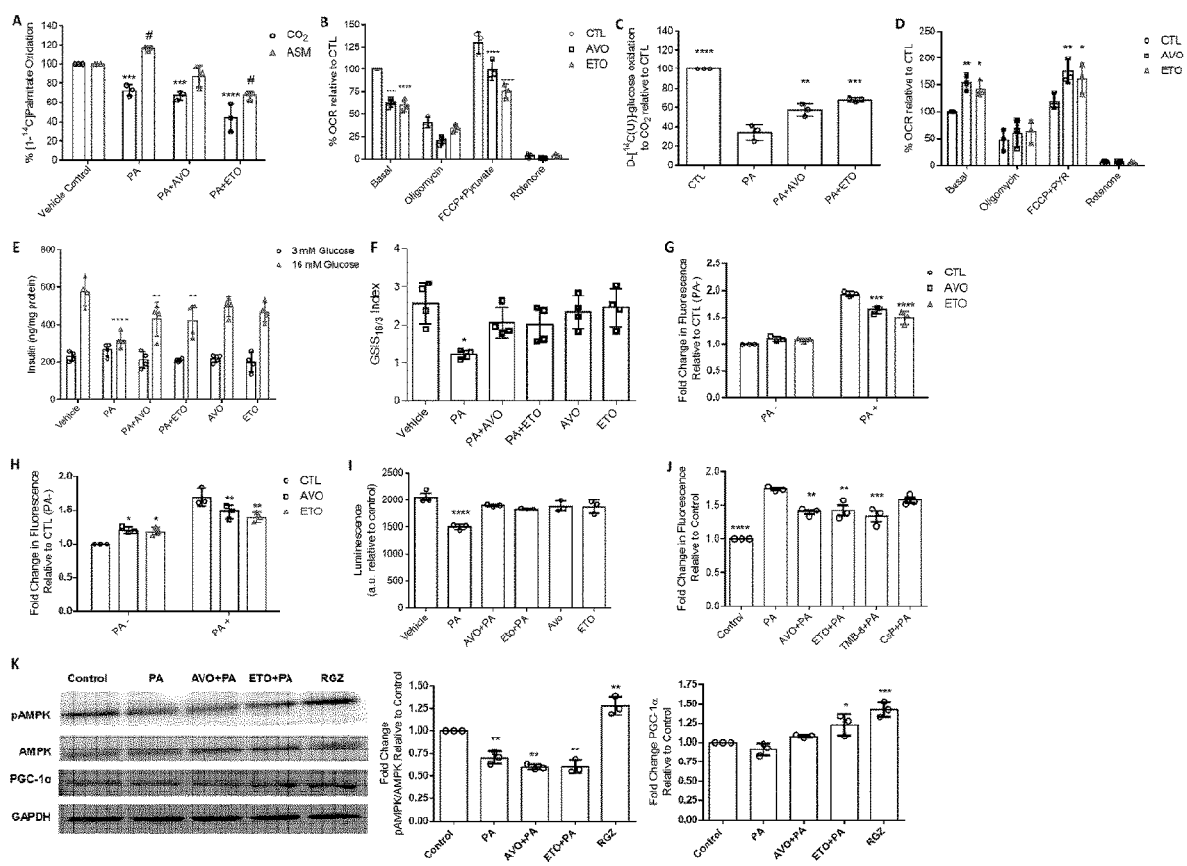
FIG. 2 illustrates the effects of AvoB on fatty acid oxidation in INS-1 (832/13) cells, which ameliorates effects of lipotoxicity and improves glucose stimulated insulin secretion. (A) INS-1 (832/13) cells were treated for 24 h with 0.5% BSA/1 mM L-carnitine (Control) or 0.5 mM palmitate-BSA/1 mM L-carnitine (PA) or PA+25 µM AVO (AVO+PA) or PA+100 µM etomoxir (ETO+PA) in low glucose (5.5 mM) media. After 24 h, fatty acid oxidation (FAO) was determined by measuring [$^{14}$C] incorporation into C02 and acid soluble metabolites (ASMs), representing complete and incomplete oxidation, respectively. (B) Palmitate supported oxygen consumption rate (OCR) was measured using high resolution respirometry (HRR) in INS-1 (832/13) cells treated as described in (A) except with 0.25 mM palmitate-BSA/1 mM L-carnitine; basal, uncoupled (oligomycin addition), and maximal uncoupled (FCCP+ pyruvate addition) respiration was assessed. (C) INS-1 (832/13) cells were treated for 24 h as described in (A) and glucose oxidation was determined by measuring [$^{14}$C] incorporation into $CO_2$ representing complete glucose oxidation. (D) To indirectly assess metabolic flexibility towards glucose utilization, oxygen consumption rate (OCR) was measured using high resolution respirometry (HRR) in INS-1 (832/13) cells treated as described in (A) except with 0.25 mM palmitate-BSA/1 mM L-carnitine for 24 h. After treatment, cells were trypsinized, collected and subjected to D-glucose addition (10 mM) for 15 min prior to HRR measurements; basal, uncoupled, and maximal uncoupled respiration was assessed as described in (C). (E) INS-1 (832/13) cells were treated for 24 h as described in (A) and GSIS assay was performed where insulin secreted into media (KRB) was quantified using an ELISA kit. Insulin in KRB was normalized to total protein content as described in the Methods section. (F) Data from (E) presented as the glucose-dependent insulin secretory index (GSIS16/3), defined as the ratio between the insulin secretion at 16 mM (stimulatory, surrogate to postprandial glucose levels) and 3 mM (basal, surrogate to fasting glucose levels) glucose. (G) Mitochondrial ROS was measured in INS-1 (832/13) cells treated as described in (A) using MitoSOX® Red. (H) Mitochondrial membrane potential was measured in INS-1 (832/13) cells treated as described in (A) using JC-1 dye. (1) Total cellular ATP content was measured in INS-1 (832/13) cells treated as described in (A). (J) Cytoplasmic Ca2+ was measured in INS-1 (832/13) using Fluo-3AM dye. Cells were treated as described in (A) and with 10 µM TMB-8 (endoplasmic reticulum calcium blocker) or 25 nM cyclosporin (mitochondrial calcium blocker) in the presence of PA. (K) Phosphorylation of AMPKα (Thr-172), and PGC-1α protein levels were assessed via western blot on INS-1 (832/13) cells treated as described in (A) and also with 2.5 µM rosiglitazone (RGZ). Figure shows representative western blots for pAMPKα-Thr172, total AMPKα, PGC-1α, and GAPDH (loading control); histograms (right) represent fold change in pAMPK and PGC-1α levels relative to vehicle control. For (A) data represent means±SEM from three independent experiments performed in triplicate. *$p<0.001$; $p<0.0001$ vs vehicle control for CO2 group or ASM group, two-way ANOVA, Sidak's post hoc test. For (B) data represent means±SEM from three independent experiments, $p<0.0001$ vs vehicle control, two-way ANOVA, Sidak's post hoc test. For (C) data represent means±SEM from three independent experiments performed in triplicate, $p<0.01$; *$p<0.001$; **$p<0.0001$ vs PA group, one-way ANOVA, Sidak's post hoc test. For (D) data represents means±SEM from three independent experiments, *$p<0.05$; $p<0.01$; vs control group, Sidak's post hoc test. For (E) data presented as mean±SEM (N=4), $p<0.01$; ****$p<0.0001$ vs vehicle control for 16 mM glucose group, two-way ANOVA, Dunnett's post hoc test. For (F) data presented as mean±SEM (N=4) *$p<0.05$ vs vehicle, One-way ANOVA, Dunnett's post hoc test. For (G-H) data are presented as mean±SEM (N=3), *$p<0.05$; $p<0.01$;*$p<0.001$; **$p<0.0001$ vs CTL (PA− or PA+) group, two-way ANOVA, Dunnett's post hoc test. For (1) data represents mean±SEM (N=3), $p<0.01$;**$p<0.0001$ vs Control, One-way ANOVA, Dunnett's post hoc test; for (J) data represents mean±SEM (N=3), $p<0.01$; *$p<0.001$; **$p<0.0001$ vs PA group, one-way ANOVA, Dunnett's post hoc test. For (K) data represents mean±SEM (N=3), *$p<0.05$; $p<0.01$; *$p<0.001$ vs Control group, one-way ANOVA, Dunnett's post hoc test.

Lipotoxicity desensitizes p-islet cells to glucose resulting in reduced GSIS and hyperinsulinemia; hallmarks of obesity and insulin resistance[16, 18-20]. To further understand the mechanism by which AvoB-induced FAO inhibition improves insulin sensitivity in vivo, we determined its effect on GSIS, generation of mitochondrial superoxide, cellular ATP levels along with cytosolic calcium levels in INS-1 cells. Lipotoxicity blunted GSIS (FIG. 2E; $p<0.0001$); a phenotype that was rescued in the presence of AvoB (FIG. 2E; $p<0.001$; FIG. 2F; $p<0.001$). AvoB also lowers palmitate-induced increases in mitochondrial superoxide levels (FIG. 2G; $F(2,12)=11.69$, $p=0.0015$); and mitochondrial membrane potential (MMP) (FIG. 2H; $F(1,12)=109.9$, $p=0.001$). AvoB restores total cellular ATP content in palmitate challenged cells compared to control levels (FIG. 2I; $F(9,20)=8.52$, $p<0.0001$). Together, these results are indicative of AvoB's ability to restore oxidative metabolism and improved efficiency of the electron transport system.

Chronic exposure to excess palmitate can alter calcium homeostasis and cause calcium leak from the endoplasmic reticulum into the cytosol which perturbs GSIS[36]. Consistent with these findings, palmitate treated cells had increased cytosolic $Ca^{2+}$ levels under non-stimulatory glucose conditions where AvoB, ETO and the endoplasmic reticulum calcium blocker, TMB-8 were able to reduce cytosolic $Ca^{2+}$ (FIG. 2J; $F(7,16)=23.08$, $p<0.0001$). These results provide direct support to the observation that in lipotoxicity GSIS was higher in the presence of the FAO inhibitors (i.e., AvoB and ETO). Lastly, the effects of AvoB in INS-1 cells were determined to be independent of AMP-activated protein kinase (AMPK) activation (FIG. 2K) and mitochondrial biogenesis, which was assessed via protein levels of PGC-1α (FIG. 2K) and/or the fluorescent dye NAO (FIG. 8A). Collectively, these results demonstrate that AVO acts as a metabolic modulator to restore GSIS in pancreatic p-islet cells under lipotoxic conditions by inhibiting FAO that improves glucose utilization, mitochondrial oxidative stress, and calcium homeostasis.

AvoB Inhibits FAO During Lipotoxicity in C2C12 Myotubes which Improves Insulin Signaling It has been reported that skeletal muscle accounts for approximately 70% of whole body glucose disposal[37]; thus, the interplay between pancreatic insulin secretion and skeletal muscle glucose utilization is a key factor in whole-body insulin sensitivity. Similar to INS-1 cells, AvoB inhibited complete FAO in C2C12 myotubes (FIG. 3A; $F(3,20)=24.64$; $p<0.0001$) and did not increase incomplete FAO as assessed by ASM levels (FIG. 3A; $F(1,20)=61.69$; $p<0.0001$). Inhibition of FAO in C2C12 myotubes was further confirmed with HRR where AvoB inhibited palmitate supported basal and maximal-uncoupled respiration (FIG. 3B; $F(6,24)=6.074$; $p<0.001$; see FIG. 7B for HRR oxygraphs). Consistent with the known effects of FAO inhibition, AvoB increased basal and insulin stimulated glucose oxidation in C2C12 myotubes in the presence of excess palmitate as measured by oxidation of D-[$^{14}$C(U)]-glucose to $CO_2$ (FIG. 3C; $F(3,16)=5.284$, $p<0.01$) and HRR (FIG. 3D; $F(2,24)=6.978$, $p<0.004$; see FIG. 7D for HRR oxygraphs).

Figure 3:
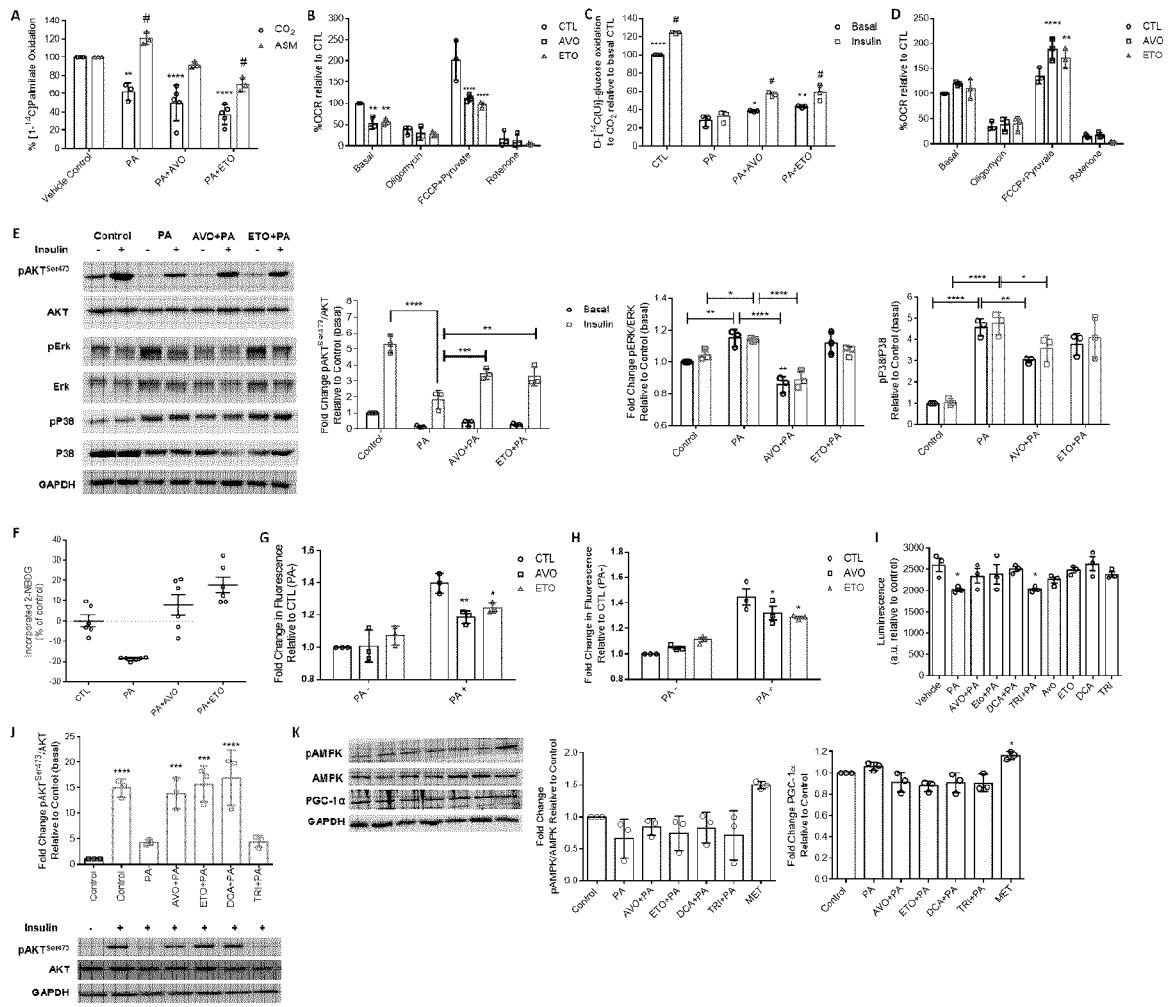
FIG. 3 illustrates the effects of AvoB on FAO in C2C12 myotubes, which ameliorates effects of lipotoxicity and improves insulin signalling. (A) C2C12 myotubes were treated for 24 h with 0.5% BSA/1 mM L-carnitine (Control) or 0.5 mM palmitate-BSA/1 mM L-carnitine (PA) or PA+25 μM AVO (AVO+PA) or PA+100 μM etomoxir (ETO+PA) in low glucose media. After 24 h, FAO was determined by measuring [$^{14}$C] incorporation into $CO_2$ and acid soluble metabolites (ASMs), representing complete and incomplete oxidation, respectively. (B) Palmitate supported oxygen consumption rate (OCR) was measured using high resolution respirometry (HRR) in C2C12 myotubes treated as described in (A) except with 0.25 mM palmitate-BSA/1 mM L-carnitine; basal, uncoupled (oligomycin addition), and maximal uncoupled (FCCP+pyruvate addition) respiration was assessed. (C) C2C12 myotubes were treated as described in (A). After 24 h, glucose oxidation was determined in insulin stimulated and non-insulin stimulated (basal) conditions by measuring [$^{14}$C] incorporation into $CO_2$ representing complete glucose oxidation. (D) Metabolic flexibility towards glucose utilization was measured using HRR in C2C12 myotubes treated as described in (A) except with 0.25 mM palmitate-BSA/1 mM L-carnitine for 24 h. After treatment, cells were trypsinized, collected and subjected to D-glucose addition (10 mM) for 15 min prior to HRR measurements; basal, uncoupled, and maximal capacity for electron flux (by FCCP-uncoupling) were then assessed. (E) C2C12 myotubes treated as described in (A) after which myotubes were starved and stimulated with 100 nM insulin for 30 min prior to lysis for Western Blot. Insulin signaling was measured by assessing phosphorylation of Akt-Ser$^{473}$. Inflammatory stress was assessed by phosphorylation of ERK1/2 and phosphorylation of P38. Figure shows representative western blots for pAkt-Ser$^{473}$, total AKT, pERK1/2, total ERK, pP38, total p38, and GAPDH (loading control); histograms (right) represent fold change in pAkt-Ser$^{473}$, pERK1/2, and pP38 relative to vehicle control (basal). (F) Insulin stimulated glucose uptake was measured using the fluorescent glucose analogue 2-NDBG via flow cytometry in C2C12 myotubes treated as described in (A). Data presented as % incorporated 2-NDBG relative to control. (G) Mitochondrial ROS was measured using Mito-SOX® Red in C2C12 myotubes treated as described in (A). (H) Mitochondrial membrane potential was measured in C2C12 myotubes treated as described in (A) using JC-1 dye. (I) Total cellular ATP content was measured in C2C12 myotubes treated as described in (A) as well as with two other metabolic modulators: 1 mM Dichloroacetate (DCA), and 25 μM trimetazidine (TRI) in the presence or absence of PA. (J) The effect of DCA and TRI on insulin signaling (pAkt-Ser$^{473}$) in C2C12 myotubes was also assessed via western blot as described for (E). (K) Phosphorylation of AMPKα (Thr-172), and PGC-1α protein levels were assessed via Western Blot on C2C12 myotubes treated as described in (A) and also with 1 mM metformin (MET). Figure shows representative western blots for pAMPKα-Thr172, total AMPKα, PGC-1α, and GAPDH (loading control); histograms (right) represent fold change in pAMPK and PGC-1α levels relative to vehicle control. For (A) data represent means±SEM from three independent experiments performed in triplicate. $p<0.01$; $p<0.0001$ vs vehicle control for $CO_2$ group or ASM group, two-way ANOVA, Sidak's post hoc test. For (B) data represent means±SEM from three independent experiments, $p<0.01$; ****$p<0.0001$ vs vehicle control, two-way ANOVA, Sidak's post hoc test. For (C) data represent means±SEM from three independent experiments performed in triplicate. *$p<0.05$; $p<0.01$; $p<0.0001$ vs PA basal group, and #$p<0.0001$ vs PA insulin stimulated group, two-way ANOVA, Sidak's post hoc test. For (D) data represents means±SEM from three independent experiments, $p<0.01$; ****$p<0.0001$; vs control group, Sidak's post hoc test. For (E) data are expressed as mean±SEM (N=4), *$p<0.05$; $p<0.01$; ** $p<0.0001$ vs basal or insulin stimulated PA group (as indicated), two-way ANOVA, Sidak's post hoc test. For (F) data presented as mean±SEM from 3 independent experiments. *$p<0.05$, $p<0.01$; * $p<0.001$ vs control, one-way ANOVA, Dunnett's post hoc test. For (G-H) data are presented as mean±SEM (N=3), *$p<0.05$; $p<0.01$; vs CTL (PA− or PA+) group, two-way ANOVA, Dunnett's post hoc test. For (I) data represents mean±SEM (N=3), $p<0.01$; **$p<0.0001$ vs Control, One-way ANOVA, Dunnett's post hoc test; for (J) data represents mean±SEM (N=3), *$p<0.001$; ****$p<0.0001$ vs Control (basal), one-way ANOVA, Dunnett's post hoc test. For (K) data represents mean±SEM (N=3), *$p<0.05$ vs Control group, one-way ANOVA, Dunnett's post hoc test.

Products of incomplete FAO have been shown to directly inhibit insulin signaling in skeletal muscle[12, 38], thus, it was evaluated if AvoB induced FAO inhibition under lipotoxic conditions in C2C12 myotubes would restore or improve insulin signaling. AvoB was able to restore the suppressive effects of lipotoxicity on insulin stimulated phosphorylation of $AKT^{Ser473}$ (FIG. 3E; $F(3,16)=11.58$; $p<0.0003$), and also reduce palmitate induced phosphorylation of mitogen-activated protein kinases (MAPK): ERK1/2 and P38 (FIG. 3E). Consistent with improving glucose oxidation and reducing the attenuation of insulin signaling under lipotoxic conditions, AVO also increased glucose uptake compared to palmitate only treated cells as measured using the fluorescent glucose analogue, 2-NDBG, which accumulates via the skeletal muscle dominant glucose transporter, GLUT 4[39] (FIG. 3F; $F(2, 17)=16.03$; $p<0.001$).

Similar to observations in INS-1 cells, AvoB lowers palmitate induced increases in mitochondrial superoxide levels (FIG. 3G; $F(2,12)=4.644$, $p<0.05$) and MMP (FIG. 3H; $F(1.12)=83.56$, $p<0.0001$) in C2C12 myotubes. AVO also restored cellular ATP content to that of control cells (FIG. 3I; $F(9, 20)=2.951$, $p=0.021$) suggesting restoration of mitochondrial function under lipotoxic conditions. Consistent with previous literature on metabolic modulation in DIO, the pyruvate dehydrogenase kinase inhibitor, dichloroacetate (DCA)[40] restored cellular ATP content (FIG. 3I) and insulin signaling (FIG. 3J) whereas the partial FAO inhibitor trimetazidine (TRI) did not exert such effects[31]. Finally, the effects of AvoB in C2C12 myotubes were determined to be independent of AMPK activation (FIG. 3K) or mitochondrial biogenesis (FIG. 3K; FIG. 8B).

Collectively, AvoB reduces the negative impact of lipotoxicity on insulin signaling in C2C12 myotubes by improving mitochondrial function and increasing glucose uptake and oxidation.

AvoB was Well-Tolerated in a Pilot Clinical Study

A Phase I pilot study (NCT03898505) was undertaken to determine the safety of the general use of AvoB. In this study, 50 or 200 mg (equivalent to consuming a quarter or one Hass avocado pulp matter) of AvoB/day or placebo was consumed for 60 days and serological and physiological assessments were measured at baseline (day 0) and days 30 and 60 (see FIG. 4A for study schematic and FIG. 9 for supplement description).

Table 2 summarizes participant baseline characteristics of participants in placebo, low dose, and high dose group at baseline.

TABLE 2

| Baseline Characteristic | Placebo | Low dose avocatin B (50 mg/day) | High dose avocatin B (200 mg/day) |
| --- | --- | --- | --- |
| Number of participants | 10 | 10 | 10 |
| Ratio of male to female (%) | 60:40 | 40:60 | 30:70 |
| Mean age (years) | 30.3 ± 10.1 | 24.4 ± 3.9 | 30.5 = 11.4 |
| Mean body weight (kg) | 74.4 ± 14.8 | 73.4 ± 15.0 | 69.8 ± 11.2 |
| Mean BMI (kg/m$^2$) | 24.3 ± 3.8 | 25.0 ± 3.6 | 22.3 ± 1.4 |
| Average hours exercise/week (h) | 4.6 ± 2.9 | 5.4 ± 3.8 | 4.6 ± 2.4 |

Table 3 summarizes adverse events (AE) across all groups. Analysis of adverse events (AE) revealed that AvoB was generally well-tolerated with minor gastrointestinal issues noted across all groups.

TABLE 3

| Adverse Event | Placebo | Low dose avocatin B (50 mg/day) | High dose avocatin B (200 mg/day) |
| --- | --- | --- | --- |
| Number of participants | 10 | 10 | 10 |
| Abdominal distention/bloating (Grade I) | 4 (40%) | 5 (50%) | 4 (40%) |
| Diarrhea (Grade I) | 1 (10%) | 1 (10%) | 1 (10%) |
| Nausea (Grade I) | 2 (20%) | 2 (20%) | 3 (30%) |
| Hand-foot skin rash (Grade I) | 0 (0%) | 0 (0%) | 3 (30%)* |

*p < 0.05 vs. placebo

Figure 4:
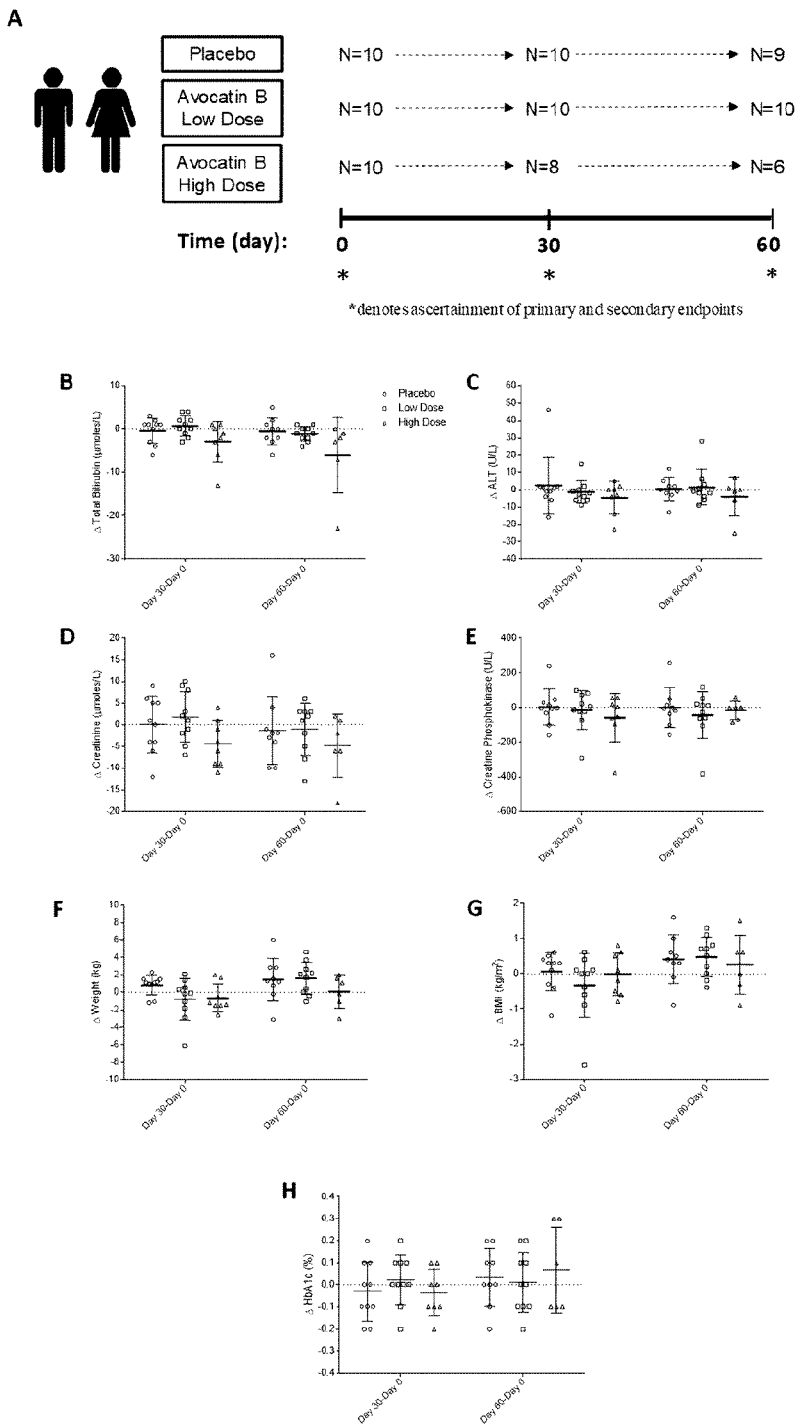
FIG. 4 illustrates the safety profile of Avocatin B after human oral consumption. (A) Schematic of clinical study design. Healthy human participants consumed placebo, low dose avocatin B or high dose avocatin B supplement once per day for 60 days. Participants dropped out of the study at different times as denoted by the "N" value at day 0, 30 or 60 of the clinical trial. Mean changes between day 30-day 0 and day 60-day 0 are presented for (B) total bilirubin, (C) alanine aminotransferase (ALT), (D) creatinine, (E) creatine phosphokinase, (F) body weight, (G) body mass index (BMI), (H) glycated hemoglobin (HbA1c). Data expressed as mean±S.D., Kruskal-Wallis—One-Way Analysis of Variance on Ranks.

Three participants in the high dose group developed a skin rash two weeks into supplementation. While this resolved after one-week of supplement discontinuation, one participant resumed supplementation to day 30 whereas two withdrew from the study prior to day 30 (see FIG. 10 for trial CONSORT diagram of participant flow). Supplementation with AvoB had no effect on several blood markers of kidney, liver, and muscle toxicity (FIG. 4B-E) or complete blood counts (FIG. 11) compared to placebo. Levels of all safety markers were within normal reference ranges as reported by the third-party diagnostic laboratory (LifeLabs Canada) that performed the blood analysis. A trend was also observed where decreases in body weight were noted in both AvoB supplemented groups between baseline and day 30 relative to placebo (FIG. 4F). Even though the trend in weight change was not statistically significant, due to the small sample size (p=0.10), it is likely that future and larger Phase II efficacy studies will be able to link human supplementation with the noted pre-clinical activity of AvoB on body weight. No clinically relevant changes from baseline in body mass index or glycated hemoglobin (HbA1c) were observed in either AvoB treated groups compared to placebo (FIG. 4G-H). Overall, the results of this pilot clinical study highlight the translational relevance, potential bioactivity and favorable safety profile of AvoB.

DISCUSSION

High dietary fat intake has been associated with insulin resistance; however, the mechanism by which excess lipids cause this pathology is still debated. Some studies have pointed to mitochondria as a potential therapeutic target to combat insulin resistance. While not wishing to be bound by any particular theory or mode of action, the results described herein suggest a shift in metabolic substrate preference as being an important mediator of insulin sensitivity. Furthermore, the results described herein support the notion that excess FAO contributes to the pathophysiology of HFD-induced insulin resistance and that FAO inhibition is a strategy in the management of DIO-induced insulin resistance.

The results described herein demonstrate that FAO inhibition following DIO-induced mitochondrial dysregulation is a viable therapeutic strategy to improve, and even restore, insulin sensitivity. The ability of AvoB to inhibit FAO, lower ROS, and improve glucose oxidation under conditions of lipotoxicity highlights the Randle Cycle as an important mediator of insulin resistance. The interplay between pancreatic β-cell insulin secretion and skeletal muscle glucose uptake is often overlooked in scientific literature, likely owing to the larger role of skeletal muscle in absorbing systemic glucose.

By the examples described herein, the effects of small molecule-induced FAO inhibition on glucose oxidation or insulin secretion in pancreatic tissue were examined. In human subjects, it was found that AvoB accumulated in both skeletal muscle (soleus and gastrocnemius) and pancreas following oral administration. While not wishing to be bound by any particular theory or mode of action, these results suggest that AvoB inhibits excessive FAO in β-cells, which improves mitochondrial glucose oxidation and restored GSIS (i.e., through improved mitochondrial function and reduced ER calcium leak). These improvements in pancreatic β-cell function along with the improved insulin sensitivity in skeletal muscle likely combine to contribute to the beneficial whole-body insulin responsiveness and glucose tolerance observed in vivo. AvoB did not impact incomplete FAO in both INS-1 and C2C12 myotubes.

AvoB also blocked palmitate-induced mitochondria-derived ROS and did not impact incomplete FAO. This further supports the favorable mechanism of action of AvoB reported herein, given previous work suggesting that lowering ROS or incomplete FAO may be relevant in reversing insulin resistance in DIO[1, 12, 15]. Collectively, inhibiting, and not accelerating, FAO through treatment with AvoB resulted in increasing glucose utilization and reversing insulin resistance.

AvoB was well tolerated in the mouse and human studies described herein. For example, in the Phase I study, where healthy human participants were given a maximum allowable dose, AvoB exerted no toxicity but did demonstrate bioactivity. AvoB was found to impart activity in both pancreatic and skeletal muscle tissue and provide a link between FAO inhibition and insulin sensitivity through increased glucose utilization and modulation of ROS. These results support the use of AvoB as a clinically-relevant alternative to conventional FAO inhibitors that impart dose-limiting toxicities, such as ETO, or pharmacological agents have little to no reported activity in pancreatic tissue and/or have a mechanism of action that is not related to FAO, such as ranolazine.

Pharmaceutical compositions of the invention may be formulated for administration orally. Therefore, the pharmaceutical compositions of the invention may be formulated, for example, as tablets, capsules, powders, granules, or liquid preparations, such as oral solutions or suspensions. Such pharmaceutical formulations may be prepared by any method known in the art of pharmacy, for example by bringing into association the active ingredient with the carrier(s) or excipient(s).

Tablets and capsules for oral administration may be in unit dose presentation form, and may contain conventional excipients such as binding agents, for example syrup, acacia, gelatine, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatine, hydroxyethyl cellulose, carboxymethyl cellulose, aluminium stearate gel or hydrogenated edible fats, emulsifying agents, for example lecithin, sorbitan, monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

It should be understood that in addition to the ingredients particularly mentioned above, the formulations may include other agents conventional in the art having regard to the type of formulation in question.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent, or patent application was specifically and individually indicated to be incorporated by reference in its entirety.

LIST OF REFERENCES CITED

[1] Anderson, E. J., Lustig, M. E., Boyle, K. E., Woodlief, T. L., Kane, D. A., Lin, C. T., III, J. W. P., Kang, L., Rabinovitch, P. S., Szeto, H. H., Houmard, J. A., Cortright, R. N., Wasserman, D. H., Neufer, P. D., *J Clin Invest* 2009, 119, 573.

[2] Després, J. P., Lemieux, I., *Nature* 2006, 444, 881.

[3] Muoio, D. M., Neufer, P. D., *Cell Metab.* 2012, 15, 595.

[4] Randle, P. J., Garland, P. B., Hales, C. N., Newsholme, E. A., *Lancet* 1963, 1, 785.

[5] Goodpaster, B. H., Sparks, L. M., *Cell Metab.* 2018, 25, 1027.

[6] Randle, P. J., *Diabetes. Metab. Rev.* 1998, 14, 263.

[7] Cline, G. W., Rothman, D. L., Magnusson, I., Katz, L. D., Shulman, G. I., *J. Clin. Invest.* 1994, 94, 2369.

[8] Kelley, D. E., Goodpaster, B., Wing, R. R., Simoneau, J.-A., *Am. J. Physiol.* Metab. 1999, 277, E1130.

[9] Cline, G. W., Magnusson, I., Rothman, D. L., Petersen, K. F., Laurent, D., Shulman, G. I., *J. Clin. Invest* 1997, 99, 2219.

[10] Roden, M., Price, T. B., Perseghin, G., Petersen, K. F., Rothman, D. L., Cline, G. W., Shulman, G. I., *J. Clin. Invest.* 1996, 97, 2859.

[11] Wolfe, R. R., *Am. J. Clin. Nutr.* 1998, 67, 519S.

[12] Koves, T. R., Ussher, J. R., Noland, R. C., Slentz, D., Mosedale, M., Ilkayeva, O., Bain, J., Stevens, R., Dyck, J. R. B., Newgard, C. B., Lopaschuk, G. D., Muoio, D. M., *Cell Metab.* 2008, 7, 45.

[13] Adams, S. H., Hoppel, C. L., Lok, K. H., Zhao, L., Wong, S. W., Minkler, P. E., Hwang, D. H., Newman, J. W., Garvey, W. T., *J. Nutr.* 2009, 139, 1073.

[14] Mihalik, S. J., *Obesity* 2010, 18, 1695.

[15] Gavin, T. P., Ernst, J. M., Kwak, H. B., Caudill, S. E., Reed, M. A., Garner, R. T., Nie, Y., Weiss, J. A., Pories, W. J., Dar, M., Lin, C. Te, Hubal, M. J., Neufer, P. D., Kuang, S., Dohm, G. L., *J. Clin. Endocrinol. Metab.* 2018, 103, 882.

[16] Zhou, Y. P., Grill, V. E., *J. Clin. Invest.* 1994, 93, 870.

[17] Zhou, Y. P., Grill, V. E., *Diabetes* 1995, 44, 394.

[18] Biden, T. J., Robinson, D., Cordery, D., Hughes, W. E., Busch, A. K., *Diabetes* 2002, 53, 159.

[19] Erion, K. A., Berdan, C. A., Burritt, N. E., Corkey, B. E., Deeney, J. T., *J. Biol. Chem.* 2015, 290, 16191.

[20] Ježek, P., Jabůrek, M., Holendová, B., Plecitá-Hlavatá, L., *Molecules* 2018, 23, 1483.

[21] Foley J E, *Diabetes Care* 1992, 15, 773.

[22] Muoio, D. M., Newgard, C. B., *Diabetes* 2008, 57, 1455.

[23] Lopaschuk, G. D., *Ann. Nutr. Metab.* 2016, 68, 15.

[24] Keung, W., Ussher, J. R., Jaswal, J. S., Raubenheimer, M., Lam, V. H., Wagg, C. S., Lopaschuk, G. D., *Diabetes* 2013, 62, 711.

[25] Gao, S., McMillan, R. P., Zhu, Q., Lopaschuk, G. D., Hulver, M. W., Butler, A. A., *Mol Metab* 2015, 4, 310.

[26] Collier, G. R., Traianedes, K., Macaulay, S. L., O'Dea, K., *Horm. Metab. Res.* 1993, 25, 9.

[27] Pettus, J., McNabb, B., Eckel, R. H., Skyler, J. S., Dhalla, A., Guan, S., Jochelson, P., Belardinelli, L., Henry, R. H., *Diabetes, Obes. Metab.* 2016, 18, 463.

[28] Lee, E. A., Angka, L., Rota, S. G., Hanlon, T., Mitchell, A., Hurren, R., Wang, X. M., Gronda, M., Boyaci, E., Bojko, B., Minden, M., Sriskanthadevan, S., Datti, A., Wrana, J. L., Edginton, A., Pawliszyn, J., Joseph, J. W., Quadrilatero, J., Schimmer, A. D., et al., *Cancer Res* 2015, 75, 2478.

[29] Buyukozturk, F., Benneyan, J. C., Carrier, R. L., *J. Control. Release* 2010, 142, 22.

[30] Guo, Z., *Proc. Natl. Acad. Sci.* 2015, 112, E2854.

[31] Kelley, D., *J. Clin. Invest.* 2005, 115, 1699.

[32] Blaak, E., Hul, G., Verdich, C., Stich, V., Martinez, A., Petersen, M., Feskens, E., Patel, K., Michel Oppert, J., Barbe, P., Toubro, S., Anderson, I., Polak, J., Astrup, A., Macdonald, I., Langin, D., Holst, C., Sorensen, T. I., Saris, W., *J. Clin. Endocrinol. Metab.* 2006, 91, 1462.

[33] Turner, N., Bruce, C. R., Beale, S. M., Hoehn, K. L., So, T., Rolph, M. S., Cooney, G. J., *Diabetes* 2007, 56, 2085.

[34] Ussher, J. R., Keung, W., Fillmore, N., Koves, T. R., Mori, J., Zhang, L., Lopaschuk, D. G., Ilkayeva, O. R., Wagg, C. S., Jaswal, J. S., Muoio, D. M., Lopaschuk, G. D., *J. Pharmacol. Exp. Ther.* 2014, 349, 487.

[35] DeFronzo, R. A., Jacot, E., Jequier, E., Maeder, E., Wahren, J., Felber, J. P., *Diabetes* 1981, 30, 1000.

[36] Zou, C., Wang, Y., Shen, Z., *J. Biochem. Biophys. Methods* 2005, 64, 207.

[37] Zhang, L., Keung, W., Samokhvalov, V., Wang, W., Lopaschuk, G. D., *Biochim. Biophys. Acta-Mol. Cell Biol. Lipids* 2010, 1801, 1.

[38] Finck, B. N., Bernal-Mizrachi, C., Han, D. H., Coleman, T., Sambandam, N., LaRiviere, L. L., Holloszy, J. O., Semenkovich, C. F., Kelly, D. P., *Cell Metab.* 2005, 1, 133.

[39] Guerre-Millo, M., Rouault, C., Poulain, P., André, J., Poitout, V., Peters, J. M., Gonzalez, F. J., Fruchart, J.-C., Reach, G., Staels, B., *Diabetes* 2001, 50, 2809.

[40] Dobbins, R. L., Szczepaniak, L. S., Bentley, B., Esser, V., Myhill, J., McGarry, J. D., *Diabetes* 2001, 50, 123.

[41] Bruce, C. R., Hoy, A. J., Turner, N., Watt, M. J., Allen, T. L., Carpenter, K., Cooney, G. J., Febbraio, M. A., Kraegen, E. W., *Diabetes* 2008, 58, 550.

[42] Sebastien, D., Herrero, L., Serra, D., Asins, G., Hegardt, F. G., Sebastian, D., Herrero, L., Serra, D., Asins, G., Hegardt, F. G., *Am. J. Physiol. Endocrinol. Metab.* 2007, 292, E677.

[43] Iglesias, M. A., Ye, J., Frangioudakis, G., Saha, A. K., Tomas, E., Ruderman, N. B., Cooney, G. J., Kraegen, E. W., *Diabetes* 2002, 51, 2886.

[44] Abu-Elheiga, L., Oh, W., Kordari, P., Wakil, S. J., *Proc. Natl. Acad. Sci.* 2003, 100, 10207.

[45] Henique, C., Mansouri, A., Fumey, G., Lenoir, V., Girard, J., Bouillaud, F., Prip-Buus, C., Cohen, I., *J. Biol. Chem.* 2010, 285, 36818.

[46] Hancock, C. R., Han, D.-H., Chen, M., Terada, S., Yasuda, T., Wright, D. C., Holloszy, J. O., *Proc. Natl. Acad. Sci.* 2008, 105, 7815.

[47] Bonnard, C., Durand, D., Peyrol, S., Chanseaume, E., Chauvin, M. a, Morio, B., Vidal, H., Rieusset, J., *J Clin Invest* 2008, 118, 789.

[48] Andersen, P., Saltin, B., *J Physiol* 1985, 366, 233.

[49] Boushel, R., Gnaiger, E., Schjerling, P., Skovbro, M., Kraunsoe, R., Dela, F., *Diabetologia* 2007, 50, 790.

[50] Holloway, G. P., Thrush, A. B., Heigenhauser, G. J. F., Tandon, N. N., Dyck, D. J., Bonen, A., Spriet, L. L., *AJP Endocrinol. Metab.* 2007, 292, E1782.

[51] Timmers, S., Nabben, M., Bosma, M., van Bree, B., Lenaers, E., van Beurden, D., Schaart, G., Westerterp-Plantenga, M. S., Langhans, W., Hesselink, M. K. C., Schrauwen-Hinderling, V. B., Schrauwen, P., *Proc. Natl. Acad. Sci.* 2012, 109, 11711.

[52] Holubarsch, C. J. F., Rohrbach, M., Karrasch, M., Boehm, E., Polonski, L., Ponikowski, P., Rhein, S., *Clin. Sci.* 2007, 113, 205.

[53] Ussher, J. R., Fillmore, N., Keung, W., Zhang, L., Mori, J., Sidhu, V. K., Fukushima, A., Gopal, K., Lopaschuk, D. G., Wagg, C. S., Jaswal, J. S., Dyck, J. R. B., Lopaschuk, G. D., *Diabetes* 2016, 65, 1883.

[54] Batran, R. Al, Gopal, K., Aburasayn, H., Eshreif, A., Almutairi, M., Greenwell, A. A., Campbell, S. A., Saleme, B., Court, E. A., Eaton, F., Light, P. E., Sutendra, G., Ussher, J. R., *JCI Insight* 2019, 4.

What is claimed is:

1. A method of treating diet-induced obesity in a subject in need thereof, the method comprising administering to the subject a therapeutically effective amount of avocatin B.

2. The method of claim 1, wherein the diet-induced obesity is associated with a metabolic disorder characterized by dysregulation of glucose-stimulated insulin secretion (GSIS) in the subject.

3. The method according to claim 1, wherein the therapeutically effective amount of avocatin B is administered in at least one daily dose.

4. The method according to claim 3, wherein the at least one daily dose is from 25 mg to 200 mg of avocatin B.

5. The method according to claim 3, wherein the at least one daily dose is about 50 mg of avocatin B.

6. A method of treating diet-induced obesity in a subject in need thereof, the method comprising administering to the subject a pharmaceutical composition comprising a therapeutically effective amount of avocatin B and a carrier.

7. The method of claim 6, wherein the therapeutically effective amount of avocatin B is from 25 mg to 200 mg.

8. The method of claim 6, wherein the therapeutically effective amount of avocatin B is about 50 mg.

9. The method of claim 1, wherein the diet-induced obesity is associated with a metabolic disorder characterized by insulin resistance in the subject.

10. The method of claim 1, wherein the diet-induced obesity is associated with a metabolic disorder characterized by reduced insulin sensitivity in the subject.

11. The method of claim 1, wherein the diet-induced obesity is associated with lipotoxicity.

* * * * *